(12) United States Patent
Taylor

(10) Patent No.: US 8,247,391 B2
(45) Date of Patent: Aug. 21, 2012

(54) GEL COMPOSITIONS

(75) Inventor: Margaret Taylor, Leicestershire (GB)

(73) Assignee: De Montfort University, Leicester (GB)

( * ) Notice: Subject to any disclaimer, the term of this patent is extended or adjusted under 35 U.S.C. 154(b) by 1428 days.

(21) Appl. No.: 10/483,313

(22) PCT Filed: Jul. 10, 2002

(86) PCT No.: PCT/GB02/03183
§ 371 (c)(1),
(2), (4) Date: Jul. 8, 2004

(87) PCT Pub. No.: WO03/006993
PCT Pub. Date: Jan. 23, 2003

(65) Prior Publication Data
US 2004/0265386 A1 Dec. 30, 2004

(30) Foreign Application Priority Data
Jul. 10, 2001 (GB) .................................. 0116860.8

(51) Int. Cl.
*A61K 31/721* (2006.01)
(52) U.S. Cl. ........................................ 514/59; 424/1.25
(58) Field of Classification Search ................. 424/1.25; 514/59
See application file for complete search history.

(56) References Cited

U.S. PATENT DOCUMENTS

| | | | | |
|---|---|---|---|---|
| 4,705,503 A | * | 11/1987 | Dorman et al. | 604/504 |
| 5,830,506 A | | 11/1998 | Taylor et al. | |
| 5,889,028 A | | 3/1999 | Sandborn et al. | |
| 5,902,607 A | * | 5/1999 | Taylor | 424/488 |
| 5,939,094 A | | 8/1999 | Durif et al. | |

FOREIGN PATENT DOCUMENTS

| | | |
|---|---|---|
| DE | 42 03 466 A1 | 10/1992 |
| WO | WO 93/13803 | 1/1993 |
| WO | WO 95/01186 | 6/1994 |
| WO | WO 98/22097 | 11/1997 |
| WO | WO 99/48419 | 3/1999 |
| WO | WO 00/09165 | 8/1999 |
| WO | WO 01/16575 A1 | 8/2000 |
| WO | WO 03/006993 A2 | 7/2002 |

OTHER PUBLICATIONS

Ballerstadt, R., and Ehwald, R., "Suitability of aqueous dispersions of dextran and concanavalin A for glucose sensing in different variants of the affinity sensor," *Biosensors & Bioelectronics* 9:557-567 (1994).

Carnali, J.O. and Naser, M.S., "The use of dilute solution viscometry to characterize the network properties of carbopol microgels," *Colloid Polym. Sci.* 270:183-193 (1992).

Kim, J.J., and Park, K., "Modulated insulin delivery from glucose-sensitive hydrogel dosage forms," *J. Contr. Release* 77:39-47 (2001).

Lee, S.J., and Park, K.., "Synthesis of sol-gel phase-reversible hydrogels sensitive to glucose," *Proceed. Intern. Syrup. Control. Rel. Bioact. Mater.*, 21:93-94 (1994).

Miyata, T., Asami, N. and Uragami, T., "A reversibly antigen-responsive hydrogel," *Nature* 9 (1999)—Abstract only.

Obaidat, A.A., and Park, K., "Characterization of protein release through glucose-sensitive hydrogel membranes," *Biomaterials* 18:801-806 (1997).

Obaidat, A.A. and Park, K., "Gel-Sol phase-reversible hydrogels sensitive to glucose," *Pharm. Research Supplemental* (1995).

Obaidat, A.A. and Park, K., "Characterization of glucose dependent Gel-Sol phase transition of the polymeric glucose concanavalin A hydrogel system," *Pharm. Research Supplemental* 7: 989-995 (1996).

Tanna, S. and Taylor, M.J., "Characterization of model solute and insulin delivery across covalently modified lectin-polysaccharide gels sensitive to glucose," *Pharm. Pharmacol. Commun.* 4:117-122 (1998).

Tanna, S. and Taylor, M.J. and Adams, G., "Insulin delivery governed by covalently modified lectin-glycogen gels sensitive to glucose," *J. Pharm. Pharmacol.* 51:1093-1098 (1999).

Tanna, S., Sahota, T.S., Clark, J. and Taylor, M.J., "Rheological characterization and insulin delivery of a novel glucose-sensitive gel with a carbomer carrier," *Sch., of Pharm. & Pharma. Sci* DeMontfort Univ, Leicester UK, 2001.

Valuev, I.L., Chupov, V.V., Sytov, G.A., Valuev, L.I. and Plate, N. A., "Phase reversible hydrogels based on Acrylamide-*N*-(2-*D*-glucose) acrylamide copolymers," *Polymer Science, Ser. B.* 39:4:156-158 (1997).

* cited by examiner

*Primary Examiner* — Fereydoun G Sajjadi
*Assistant Examiner* — Danielle Sullivan
(74) *Attorney, Agent, or Firm* — Montgomery, McCracken, Walker & Rhoads, LLP; Evelyn H. McConathy

(57) ABSTRACT

The present invention relates to a gel composition, comprising first and second gel-forming moieties which bind reversibly to one another to form a gel. The binding of the moieties is sensitive to the level of an analyte, and either or both of the gel-forming moieties are attached to cross-linked particulate entities such that the interstices between the entities allow gel-sol and sol-gel transformation, and yet are not so small that the analyte cannot diffuse therethrough. The invention also provides drug delivery systems and sensors for detecting an analyte utilizing such a gel.

2 Claims, 14 Drawing Sheets

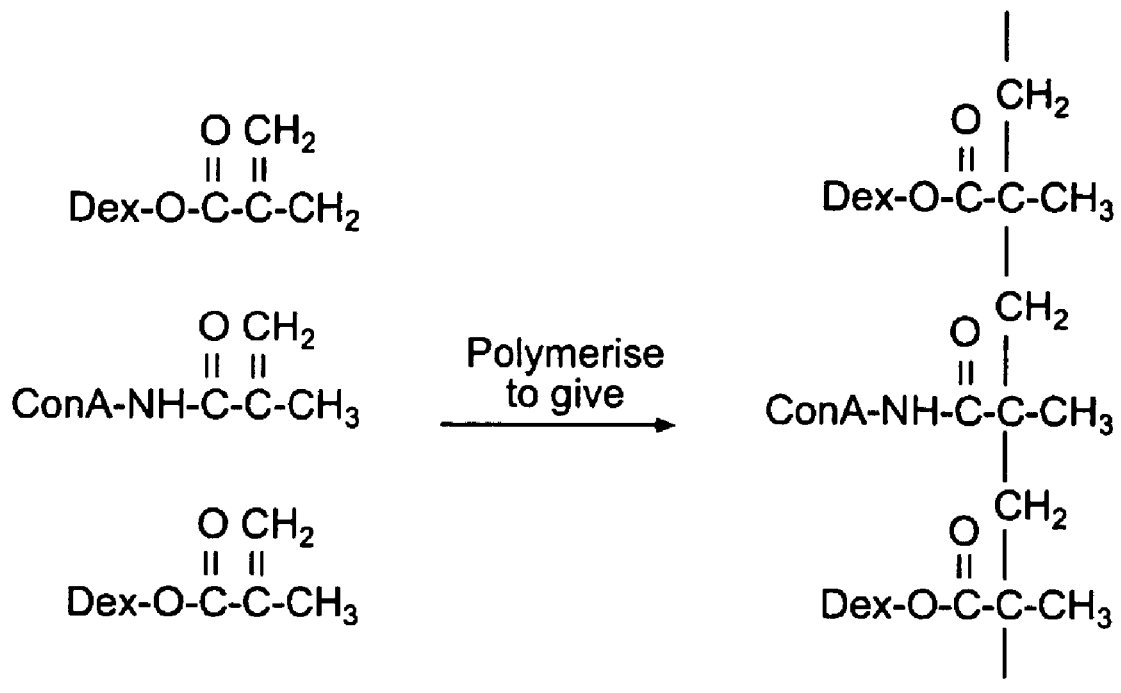
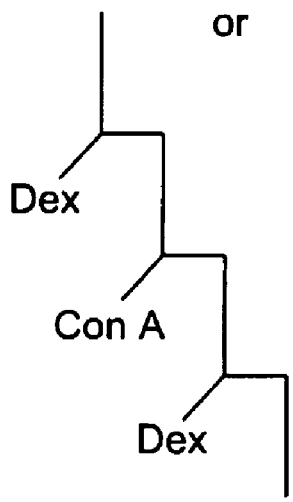
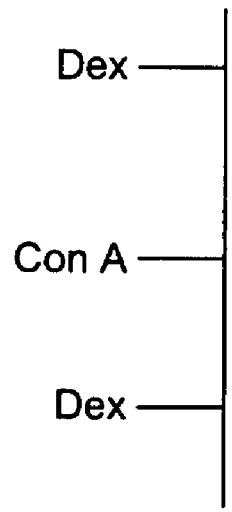
Fig. 1 a) Large solutes such as insulin can diffuse through interstices b) carbomer C974 or C934 with lectin covalently bound to surface c) Dextran multivalent for terminal glucose moieties

Fig. 7a d) Lectin (con A) covalently bonded to carrier carbomer and mixed with dextran (not carrier bound in this particular case), the interstitial regions become glucose sensitive but remain large enough to transport insulin

Fig. 7b

Graph 12 (Study 3.1) (mixture 32) Comparison of loss tangent values for the 2%C974-8% gelatin mixture with 0% chymotrypsin. Taken at 37°C Study 14 (Study 3.1) (mixture 2) Comparison of loss tangent values for the 2%C974-8% gelatin mixture with 0.1% chymotrypsin. Measured at 20°C

GEL COMPOSITIONS

BACKGROUND OF THE INVENTION

The present invention relates to gel compositions which comprise gel-forming moieties which bind to one another to form a gel. The binding of the gel-forming moieties is dependent on the level of a specific analyte and may be reversible. Such gels find use in monitoring the level of the analyte in a sample and delivering drugs in response to abnormal levels of the analyte.

In the prior art, WO 93/13803 discloses a gel which, in one embodiment, comprises dextran and concanavalin A (ConA). Terminal glucose residues of dextran bind to ConA, resulting in the formation of a higher viscosity gel. Reversal of this binding occurs when free glucose competes with the dextran glucose residues for binding to ConA. Thus, the gel is sensitive to the amount of free glucose with which it is brought into contact. As such, the gel can be used as a drug delivery system using an anti-hyperglycaemic drug such as insulin. In normal levels of glucose, dextran binds ConA and the gel retains the insulin therein. However, when the level of glucose rises, the degree of binding falls, releasing the insulin. In a physiological situation, the release of insulin will result in the level of glucose falling and the degree of binding will increase, thereby preventing release of further insulin. Thus, the drug delivery system forms a "closed loop" system which has the same effect as a normally-functioning pancreas, with insulin being released when required (when glucose causes the gel to undergo gel-sol transition) and retained when not required (when the lack of glucose causes the gel to undergo sol-gel transition).

Similar gels are disclosed in Obaidat & Park, *Biomaterials* 18 (11 1997): 801-806; Obaidat & Park, *Pharmaceutical Research* 12 (9 SUPPL 1995); Obaidat & Park, *Pharmaceutical Research* 13 (7 1996): 989-995; and Valuev, et al, *Vysokomolekulyarnye Soedineniya Seriya A & Seriya B* (1997): 751-754.

A gel of this type is disclosed for use as a glucose sensor in DE-A-4203466. The gel is located in a semi-permeable tube such that the change in viscosity of the gel resulting from the reversible gel-sol change causes the gel surface to respond to an oscillation signal. The degree of response depends on the viscosity of the gel and hence the concentration of glucose. Later work describes the response of such a gel to glucose as measured by surface plasmon resonance (SPR) to measure the kinetics of the response rather than the viscosity itself (Ballerstadt & Schultz, *Sensors and Actuators B Chemical*, (1998), 46: 557-567). Rather than producing a gel, a lectin was immobilised on a surface and the displacement of fluorescent labelled lectin was measured with laser optics. Thus, this later work did not use the change in viscosity as a measure of glucose levels. Similarly, DE-A-4034565 describes the measurement of radioactive lectin from cross-linked dextran beads.

Finally, WO99/48419 describes the use of a viscosity-sensitive chip to measure the change of viscosity of a reversible gel (specifically a Ficoll-ConA gel) to determine the level of glucose in a sample to be analysed.

A problem of gels of this type is that they are water-miscible and hence are prone to dispersal. This problem becomes particularly acute if they are used in vivo to detect a particular analyte, because the components of the gel could cause an unwanted immune reaction: indeed, ConA is mitogenic. For this reason, the gels may be enclosed by a semi-permeable membrane which will allow passage of the analyte into contact with the gel. However, in order for the gel to react to changed levels of analyte within a reasonable time, the analyte must be able to pass quickly through the semi-permeable membrane. In addition, in those situations where a drug is to be released, the membrane must allow quick release. To ensure such quick passage, the membrane needs to have relatively large openings and/or be relatively thin, with the result that the components of the gel can leach through the semi-permeable membrane. For example, a gel of the type described in WO 93/13803 is water-miscible and must be confined in a small pore membrane to prevent rapid dispersal of the gel-forming components, especially in the sol form induced by raised levels of glucose. However, pore sizes (e.g. 0.1 µm) which are not rate-limiting for release of the 36 kD insulin hexamer still allow the 10 kD ConA tetramer and, to a lesser extent, dextran to escape.

It is therefore desirable to produce a gel of the type described above which is less prone to dispersal.

According to the present invention, there is provided a gel composition comprising first and second gel-forming moieties which bind reversibly to one another to form a gel, wherein said binding is sensitive to the level of an analyte, and either or both of the gel-forming moieties are attached to cross-linked particulate entities such that the interstices between the entities allow gel-sol and sol-gel transformation, and yet are not so small that the analyte cannot diffuse therethrough.

DESCRIPTION OF THE DRAWINGS

The following detailed description of the invention will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

The invention will be described with reference to the accompanying drawings, in which:

FIG. 1 illustrates the polymerisation of methacrylate derivatives of dextran and con A;

FIG. 7 illustrates structures and insulin diffusion pathways before and after grafting con A to carbomer particles surfaces;

DESCRIPTION OF PREFERRED EMBODIMENTS OF THE INVENTION

Figure 2:
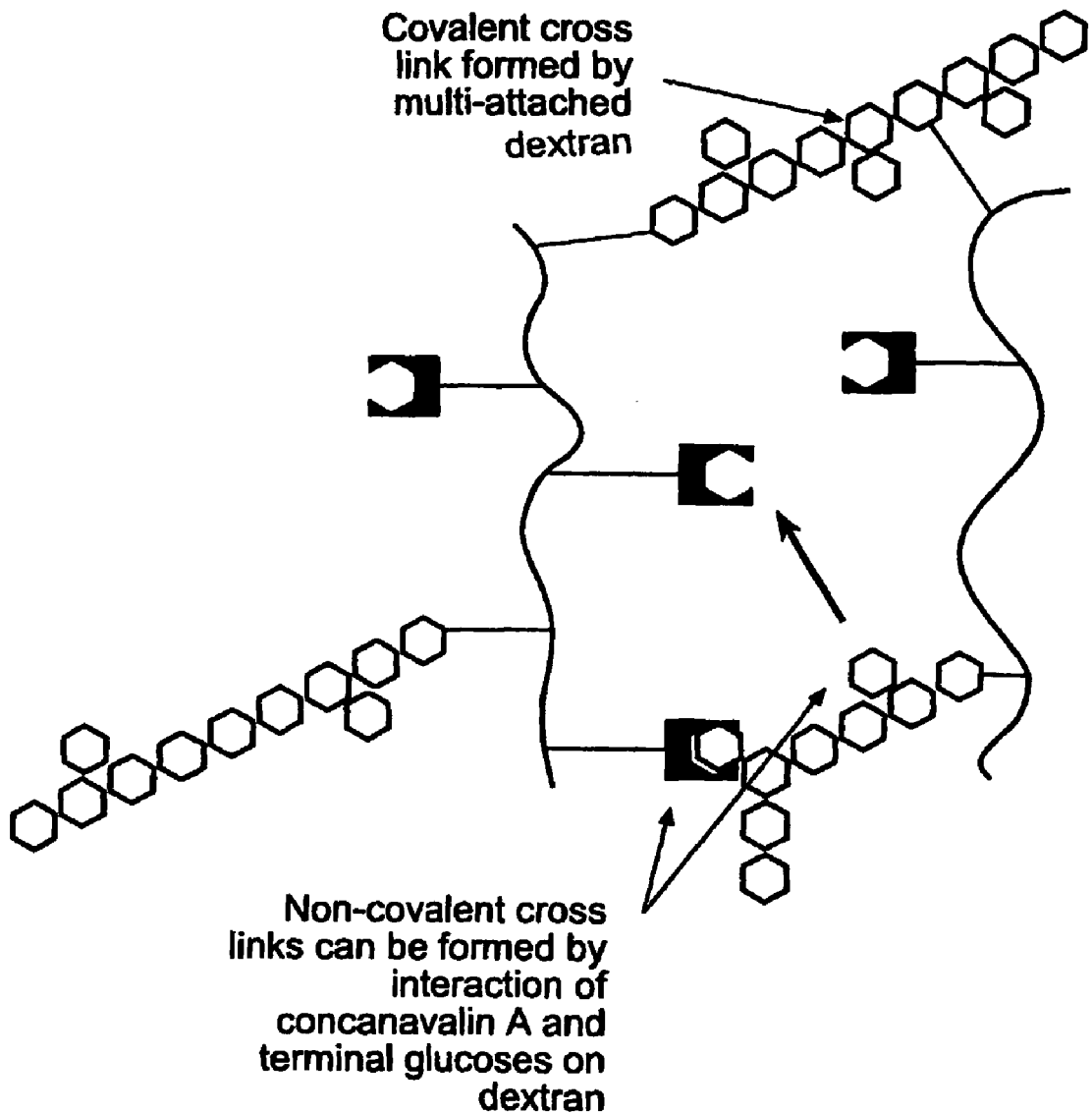
FIG. 2 is a diagrammatic representation of a dextran-con A copolymer resulting from the polymerisation of methacrylate derivatives of dextran and con A.

The present invention provides a reversible gel in which the interactive ligand pair (the first and second moieties) are retained within the gel (i.e. their leach to the surroundings is prevented). In addition, the phase separation of the components during the liquid stages of the gel-sol cycles is prevented, thus ensuring the juxtaposition of the first and second moieties and increasing the life of the composition. Preventing phase separation is also important because it fosters the continuing probability of interaction between the relevant ligands.

Preferred particulate entities are polymers which are locally cross-linked such that they form particles, sometimes known as "microgels", "minigels" or "fuzzballs", in which each particle is a discrete hydrogel structure which is substantially or completely surrounded by an aqueous interstitial region. It is preferred if the degree of cross-linking is greater than that in Carbopol 941, which has 1 linker for every 3300 monomers (Carnali & Naser, 1992, *Colloid Polymer Sci.* 270: 183-193).

In certain embodiments of the invention, the particulate entities have a mean diameter of 150 or 100 µm or less, preferably in the range of from 10 to 80 or 20 to 70 µm, as this may prevent the composition from crossing a membrane with pore sizes of 0.1 mm and above, and yet allows easy passage of the analyte and, when present, a drug which may have to pass through the composition.

In a preferred embodiment, the cross-linked polymer is an acrylic acid polymer or copolymer and is preferably a cross-linked carbomer (also known as Carbopol (BFGoodrich (USA), polycarbophil, carboxyvinyl or carboxypolymethylene polymer).

Acrylic acid is a small molecule with a reactive double bond capable of polymerising into linear arrangements with pendant ionisable carboxyl groups remaining from each monomer. This produces hydrophilic products capable of behaving as polyelectrolytes. The linear derivatives of this type (such as Carbopol 907) are reported as having an average molecular weight of 500,000 and are water soluble. Various degrees of cross linking can also occur. Both the degree and type of cross linking has given rise to a large range of polymers, many of which incorporate other monomers besides the acid. For example, some Carbopols and Pemulens (BFGoodrich) consist of acrylic acid copolymerised with long chain alkyl residues and are cross linked with allyl pentaerythritol. Polycarbophils (marketed as Noveon) are homopolymers of acrylic acid loosely cross linked with divinyl glycol.

Cross-linked carbomer homopolymers are characterised by being cross linked to various extents with polyalkyl polyethers. Some are pharmaceutically more-acceptable either because of the solvent system used in polymerisation or because they contain dispersal facilitators, but the intended utility is a function of cross link characteristics as described. Most types are produced as dry powders which comprise particles which maintain their integrity when dispersed in water. Each particle is an agglomerate of inseparable smaller components but the molecular weight of the primary particles is, in effect, in billions, with each linear chain being connected by the cross linker arrangements, to many others, forming one large molecule. The average diameter of the dry aggregate is generally 2-7 µm, which increases tenfold as the structures swell on hydration and neutralisation. The latter process produces a gelatinous product which appears to be homogeneous but in fact comprises the individual swollen particles separated by aqueous interstitial regions.

Dissolved material percolates both through and between the gelatinous particles of the gel. Permeability of a solute through carbomer gel dispersions is a function of the cross-linking density because the more tightly meshed particle interiors exclude diffusing solutes on a size basis much like a conventional beaded gel permeation system like Sephadex, except that the beads are smaller and less rigid. Many substances travel through carbomer gels much faster, therefore, than through other homogeneous gels, such as hypromellose, even when macroviscosity is matched. Carbomers have therefore been used widely to control the delivery of many solutes through a hydrated layer and are included in many tablet formulations for this purpose often as comparisons with linear polymers which release by erosion. In addition, carbomers have been found to adhere strongly to mucus and have been investigated for binding drug delivery structures to the gut, the eye and the nasal mucosa in order to prolong dosage.

Preferred carbomers are Carbopol 974P, which has a tightly cross-linked structure (with allyl pentaerythritol) causing each hydrated particle to be relatively rigid and to remain discrete from its neighbours, and Carbopol 934P, which is less cross linked (with allyl sucrose). Because these carbomers are cross-linked extensively but regionally, they are particulate; even when they are hydrated they form flexible, small (20-70 µm in $H_2O$) beads. These beads will not allow the diffusion of large molecules through them but only around them.

Cross-linked carbomer particles have many qualities that make them attractive as carriers for proteins and other biologically active moieties.

- the particles have pendant carboxyl groups, many of which are externally oriented. These enable the covalent attachment of active entities including proteins, peptides and other agents bearing active moieties such as amine groups by generic and specific means including carbodiimide chemistry.
- the particles are polyelectrolytes and are highly ionised at neutral pH, enabling electrostatic attachment of suitable cationic ligands.
- some proteins have non-specific attraction for polyacrylic acid and hence may not have to be covalently attached. For example, at low pH (<4), there is a very strong physical attachment between concanavalin A and carbomers which needs no covalent bonding (mixtures of solutions form a precipitate) and which is independent of the glucose receptor. Because of the low pH required, it is preferred that one or both of the gel-forming moieties is/are attached covalently to the particles. In a preferred embodiment of the invention, cross-linked carbomers are used as carriers in concanavalin A/dextran gels as an additive. This produces a clear gel which responds very well and yet effectively prevents the leach of protein as outlined above.

the covalent and electrostatic attachment of ligands can be in very large numbers, again because of the high incidence of carboxyls.

the polyanionic nature of carbomer means that it can be dehydrated in low pH media. This allows it to be centrifuged and thus separated from extraneous material left from coupling procedures. It can be repeatedly washed and spun in this form and finally rehydrated by neutralising in suitable buffer or other aqueous media.

carbomers can carry certain types of solutes inside the particle in addition to the same or other entities being present on the external surface. Thus, for example, a therapeutic agent can be held within the particle, whether bonded there or not, while a targeting and/or stealth-type entity could be grafted onto the exterior surface.

carbomers are very large by comparison with other carriers and although unsuitable for some therapeutic purposes for this reason (for example it would not extravasate), becomes more potentially useful for others. Thus, following delivery, the conjugate may remain longer at the target site as excretion, metabolism and degradation proceed more slowly than with smaller entities. Such a carrier could, for example, have much in common with liposomes, which are of similar size and have long been used as experimental drug delivery agents. Carbomers offer a greater capacity for covalent attachment than is the case for liposomes, however. As with liposomes, carbomers could be modified covalently by the addition of polyethylene glycol (among other hydrophilic neutral polymers) to provide a surface with steric and other properties which prevent uptake by macrophages in the large vessels of the liver and spleen.

being particulate, cross-linked carbomers can function in the manner of an exclusion gel and therefore many solutes percolate around rather than through the particles (or beadlets) of hydrogel. Diffusion through carbomer gels is therefore governed by the microviscosity of the aqueous medium in the interstitial regions and is much faster for many solutes than for similar consistency but homogeneously cross-linked hydrogels, where the solute migration is a function of the macroviscosity. Where beadlets have then been surface-modified as carriers for covalently bound ligands, the ligands can affect the microviscosity of the interstitial regions. This region can therefore interact with solutes chemically or physically. Thus, a gel bed could act as an affinity substrate for solutes in designs for chromatographic separation, substrate sensors and intelligent delivery devices.

There is a number of variations in which the first and second moieties can be attached to the particles. For example, the particles can have either the first or the second moieties attached (covalently or otherwise) directly thereto, or can have both the first and second moieties directly attached (covalently or otherwise) thereto. Alternatively or additionally, instead of being directly attached, the first and/or second moieties can be indirectly attached via a polymer. Suitable polymers are known to the skilled person and include acrylic backbone polymers, dextrans, celluloses and other sugar polymers. The first and second moieties can be attached to each other (e.g. in the manner described in WO95/01186) with one or other being directly or indirectly attached to the particles.

The first and second moieties can be any moieties which can bind reversibly together to form a gel. It is preferred if the first moiety is a macromolecule which, when bound together, forms a gel and the second moiety is a molecule which binds to at least a part of the macromolecule to provide such binding. However, both the first and second moieties could contribute equally to gel formation. Preferably, the sensitivity of the gel to the level of said analyte arises because the second gel-forming moiety also binds to the analyte. Thus, the analyte competes with the first gel-forming moiety and, when the concentration of the analyte is sufficiently high, will prevent binding of the first and second gel-forming moieties, resulting in a decrease in the viscosity of the gel. As is described in more detail below, this decrease in viscosity can be used to release a drug or to provide an indication of the level of the analyte.

Bonding between the first and second moieties is caused by non-covalent forces such as hydrophobic, ionic, hydrogen bonding forces and the like. These interactions have been well studied in the art and their effects on molecular affinity and recognition are described, for example in Korolkovas et al, "Essentials of Medicinal Chemistry", pp 44-81 Wiley, 1976. Such reversible interactions are exemplified by the interaction between an enzyme and its substrate or a competitive inhibitor thereof; and antibody with its antigen, or a drug receptor site and its drug.

The second moiety may be any of a number of well-known entities which exhibit molecular recognition and reversible binding of micro- or macromolecules. The second moiety may be a natural binding protein, such as an antibody, an enzyme, a regulatory protein, a drug receptor site or the like. It is also possible to use synthetically modified binding molecules, such as chemically modified proteins. Such modified proteins sometimes have increased or decreased affinities for their substrates when compared to their natural unmodified counterparts. The second moiety may be a receptor built by imprinting and similar techniques (Andersson, *J Chromatogr B Biomed Sci Appl.* 2000 Aug. 4:745(1):3-13; Bruggemann et al, *J Chromatogr A.* 2000 Aug. 11; 889(1-2):15-24; Haupt & Mosbach, *Trends Biotechnol* 1998 November; 16(11):468-75).

It is preferred is the second moiety is a lectin. Lectins are carbohydrate-binding proteins of plants and animals with a wide variety of specificities for carbohydrates, (Lis et al, *Ann. Review of Biochemistry,* 42, 541 (1973); Goldstein & Hayes, *Adv. in Carbohydrate Chemistry and Biochemistry,* Vol. 35, Tipson and Horton, eds. (Academic Press, New York, 1978, pp. 128-341). For example, ConA, a Jack Bean lectin, has specificity for α-D mannopyranose and α-D glucopyranose; soybean lectins are specific for α- and β-D-N-acetylgalactosamine and α-D-galactose units, and wheat germ lectin is specific for β-D-N-acetyl glucosamine. Another lectin that may be used in the present invention is the pea (*Pisium sativum*) lectin. In a preferred embodiment, the second moiety is a lectin, and the first moiety is a gel-forming macromolecule which binds to the lectin and which may be a carbohydrate polymer, preferably containing glucose, fructose or mannose moieties, such as branched starches, dextrans, mannans, and levans, or synthetic carbohydrates such as ficoll-400, a synthetic polysucrose, or a synthetic polymer with pendant carbohydrate or sugar moieties.

In one embodiment, blue dextran is used (Sigma). This is available in two molecular weights (40 K and 2 M), and comprises dextran covalently bonded to reactive blue. Each dextran molecule has many dye moieties bonded to it, and the molecule is blue and has free amine groups from the dye which are available for coupling. When coupling is done with blue dextran, the product is blue. This provides a qualitative and quantitative assessment of the success of coupling.

The first and second moieties may be provided in the form of a copolymer. This may be made by polymerising prepared derivatives of the first and second moieties. At its simplest, this can make a linear polymer bearing both moieties. Any type of polymer backbone produced by any relevant polymerisation technique is suitable for use in this embodiment of the present invention.

In a second aspect, the invention provides a gel composition comprising first and second gel-forming moieties which bind reversibly to one another to form a gel, wherein said binding is sensitive to the level of an analyte, and the gel-forming moieties are copolymerised.

In one embodiment, the methacrylate derivatives of concanavalin A and dextran (synthesised first from the raw lectin and polysaccharide, using a reaction with methacrylic anhydride) are polymerised to make an acrylic backbone polymer, carrying the concanavalin A and dextran as pendants (see FIG. 1).

Dextran is capable of methacrylate derivatisation (i.e. in the pre-polymerisation stage with methacrylic anhydride) at many points along its length, the number depending on conditions, since each hydroxyl group of every glucose unit in the dextran chain, is potentially susceptible to methacrylation. Accordingly, dextran moieties can permanently cross link the linear copolymer, producing a range of three-dimensional networks simply because it can start forming polymer chains at any point at which it has a methacrylate modification. Unless the degree of cross linking is very high, the ensuing products are likely to be flexible and gelatinous because of the length and mobility of dextran. Concanavalin A can also be multi-methacrylated, but because this molecule is globular, the product may be an aggregate and not a gel in which flexible networking extends throughout (see FIG. 2).

The fundamental character of products made by a polymerisation process such as the one described above is hydrophilic, but, in cases where the polymerisation product becomes too large and complicated to remain soluble, the product merely swells in water and does not form a solution (soft contact lenses are made from a non-derivatised version of such an acrylic). The permanent links dictate the major characteristics of the product in terms of its viscoelastic qualities, and so those products which have less derivatisation of the dextran and concanavalin A (for example) will be viscous liquids, while those which have extensive modification and thus allow complicated cross linking, will be solid hydrogels.

Figure 3:
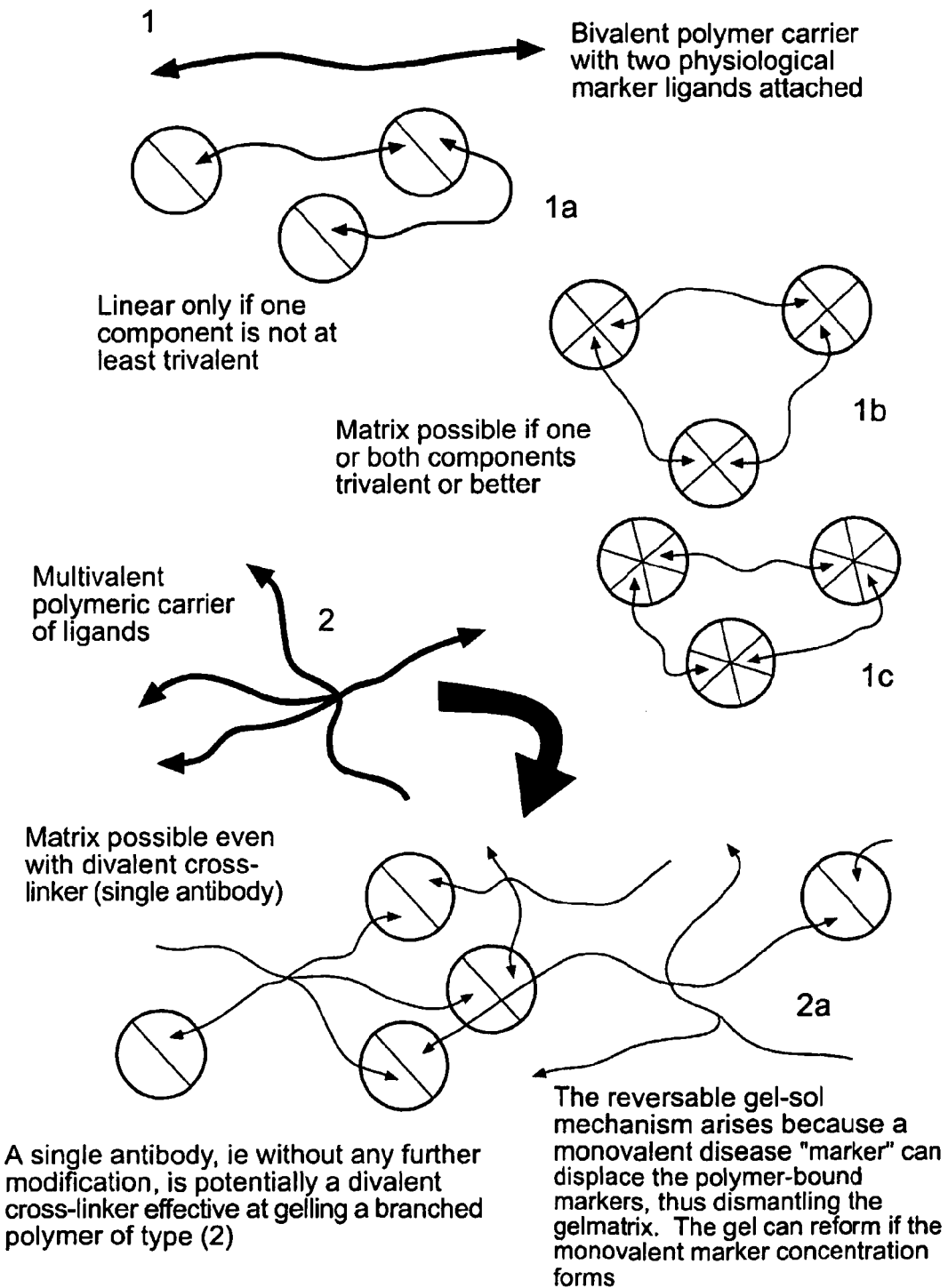
FIG. 3 illustrates how a matrix can be formed when at least one of the components of the matrix is at least trivalent.

However, the interactive ligands are able to connect across the polymer chains non-covalently producing temporary bonding additional to any permanent bonds made during polymerisation (see FIG. 2). It is these which are crucial in terms of the reversible binding of the gel because, when in contact with the analyte, e.g. free glucose, the temporary bonds will be dismantled. When this happens, there will be a change in the properties of the product and it will become more permeable, as the notional pores throughout the lattice open up and leave only the permanent cross links. If the derivatisation and consequent permanent cross linking of the gel has been appropriately low, a viscous liquid can result when all of the permanent and temporary linking is in place. When the analyte is added, this liquid will lose viscosity and, because the reaction is reversible, this gel-sol change can be dependent on the concentration of analyte that has diffused into the gel.

Where the first and second gel-forming entities are not copolymerised, each component is multivalent in order that a three dimensional network or matrix results (and at least one component must have a valency greater than two, since two divalent interactants produce a linear arrangement). This is illustrated in FIG. 3.

In a gel comprising lectin and dextran which are not attached to one another or to other particles, the lectin is in its naturally tetravalent form which can dissociate into stable dimers at some pH values. These dimers are obviously smaller and are at a greater risk of loss from the gel. The combination of the tetravalent concanavalin A and the multivalent (branched) dextran produces a gel, which consists of a three dimensional network stabilised with only temporary bonds. However, the components can gradually leach away when in the sol state: phase separation may not be obvious but may contribute to progressive loss of action after several cycles.

Figure 4:
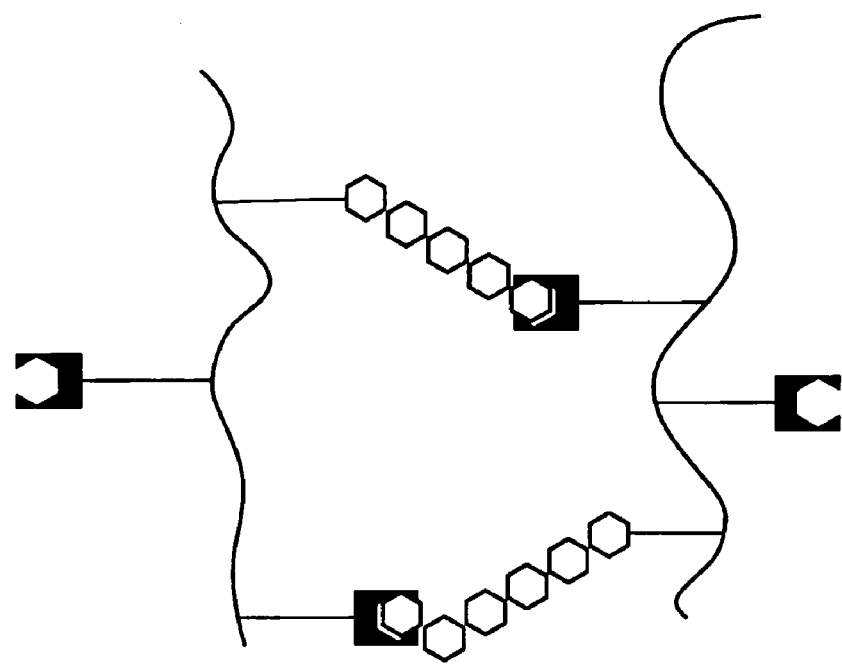
FIG. 4 is a diagrammatic representation of a gel in accordance with the present invention.
Figure 5:
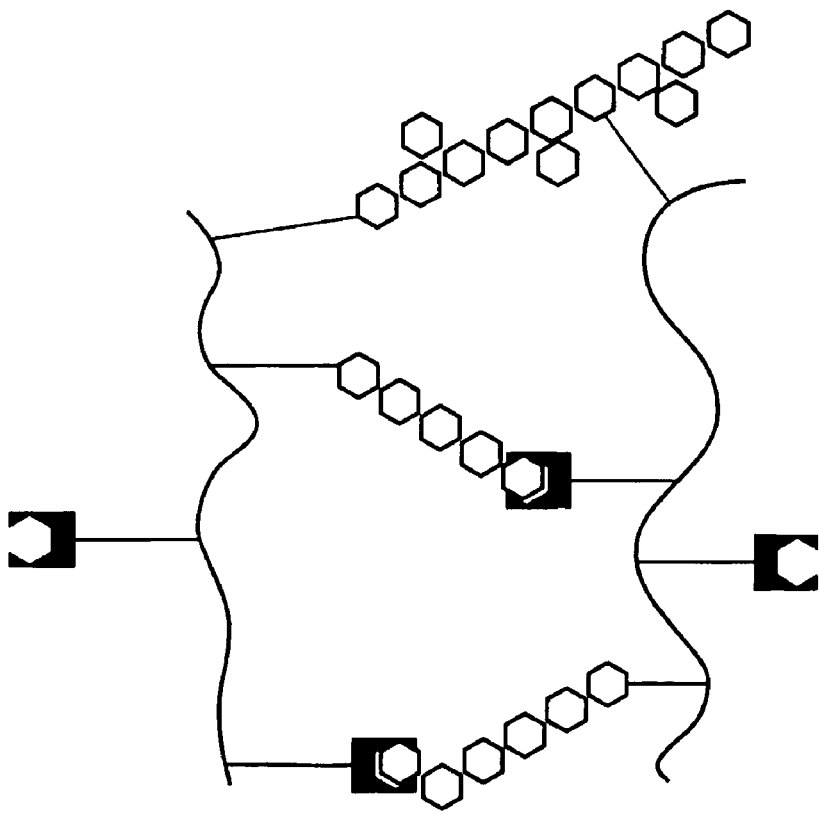
FIG. 5 is a diagrammatic representation of another gel in accordance with the present invention.
Figure 6:
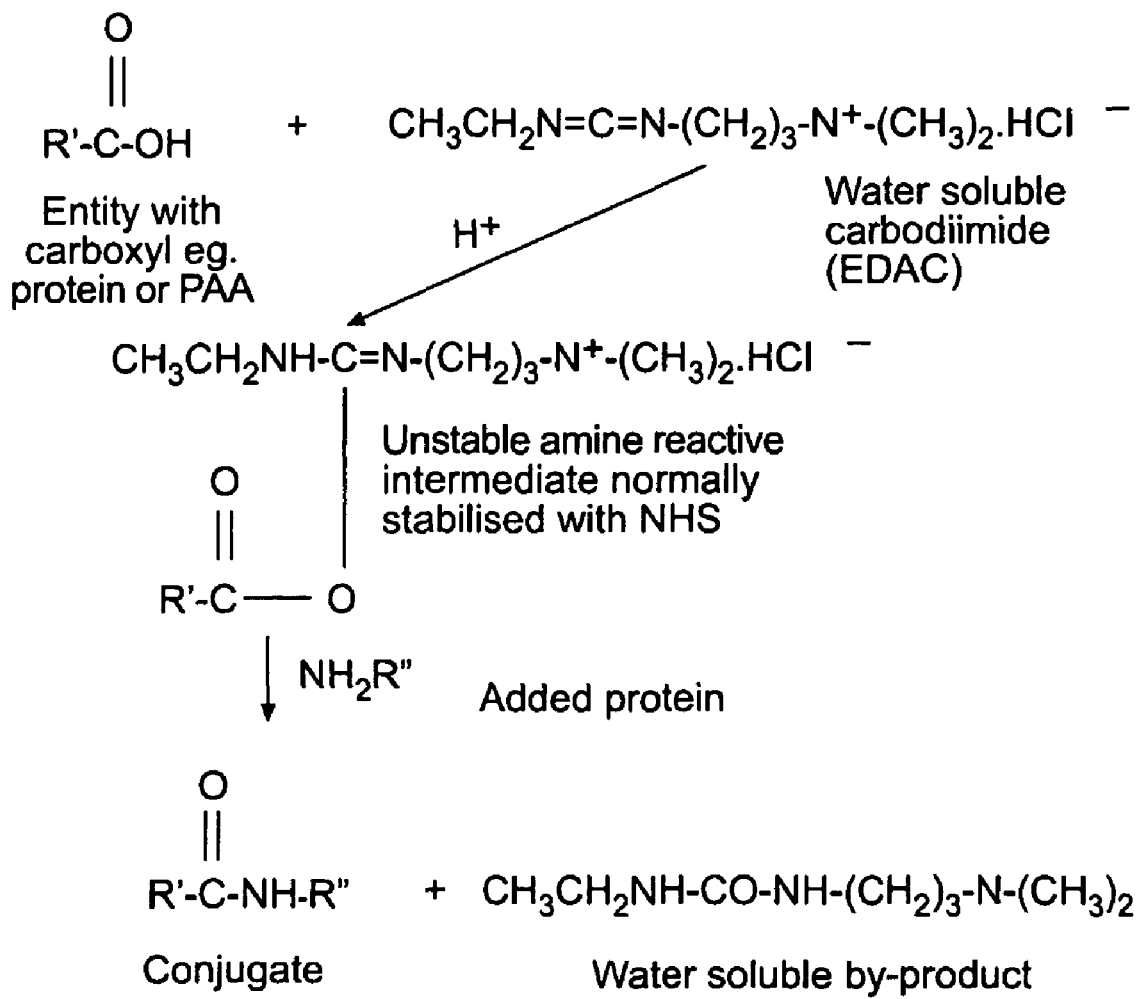
FIG. 6 illustrates the carbodiimide addition of amine containing entity, such as con A, to a carboxyl bearing carrier, such as carbomer.

However, when the interactive components are copolymerised or attached to particles, each component could be monovalent, and this would still form a gel, as illustrated in FIG. 4. Accordingly, the gel of the present invention does not require first and second gel-forming moieties which are multivalent. In a preferred embodiment, lectin dimers (or tetramers stabilised by binding onto the framework) can be used. Dextran may be substituted with a variety of other glucose bearing entities, including simple pendant glucose. However, single pendant glucose may reduce the flexibility of the resulting gel and in fact, some permanent cross linking with dextran might be remain useful to give flexibility and prevent leaching away in the sol phase. This is shown in FIG. 5.

As mentioned, the second moiety may be an antibody. Antibodies can be prepared and purified from animals in standard fashion (Eisen, H. N. "Immunology", Harper & Row, 1974), and have the advantage of being induceable in an animal by challenge with an appropriate antigenic agent. Since this agent can be chosen from any chemical family e.g., amino acids, carbohydrates, their respective polymeric derivatives, or the like, the resulting antibodies may have a wide range of binding specificity and affinity.

Polyclonal antibodies can be raised by stimulating their production in a suitable animal host (e.g. a mouse, rat, guinea pig, rabbit, sheep, goat or monkey). Monoclonal antibodies can be produced from hybridomas. These can be formed by fusing myeloma cells and spleen cells which produce the desired antibody in order to form an immortal cell line. This is the well known Kohler & Milstein technique (*Nature* 256 52-55 (1975)). Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London. In addition to whole antibodies, the present invention may use derivatives thereof, including antibody fragments and synthetic constructs. Examples of antibody fragments and synthetic constructs are given by Dougall et al in *Tibtech* 12 372-379 (September 1994). Antibody fragments include, for example, Fab, F(ab')$_2$ and F$_v$ fragments (see Roitt et al [supra]). F$_v$ fragments can be modified to produce a synthetic construct known as a single chain F$_v$ (scF$_v$) molecule. This includes a peptide linker covalently joining V$_h$ and V$_1$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains. Synthetic constructs include chimaeric molecules. Thus, for example, humanised (or primatised) antibodies or derivatives thereof could be used. An example of a humanised antibody is an antibody having human framework regions, but rodent hypervariable regions.

An example of a suitable antigen and antibody is angiotensin (Peeters, et al, *J Immunol Methods* 120 (1 1989): 133-43) and an anti-angiotensin antibody (available from Sigma, for example). A gel formed by these would be responsive to free angiotensin, which is involved in hypertensive crises. Thus, the gel could be used to monitor levels of free angiotensin and/or govern the release of angiotensin conversion enzyme (ACE) inhibitors, such as enalapril, which would treat the hypertensive crises, avoiding the need for continuous medication.

Some hormone-dependent tumours are treated with hormone antagonists like tamoxifen and cyproterone. The automatically-regulated delivery of such drugs in response to endogenous hormone peaks might offer an alternative to either their blanket use, which is strongly linked to toxic effects, or to the use of agents such as goserelin (which interfere with natural feedback in hormone biosynthesis and can paradoxically increase symptoms by doing so). Thus, a gel formed from testosterone and anti-testosterone antibody (Miyake, et al, *Chem Pharm Bull* 38 (4 1990): 951-5) could be used to deliver cyproterone for prostate cancer.

Another example is morphine and anti-morphine antibody (Kussie, et al, *J Immunol* 146 (12 1991): 4248-57) which could used to deliver a morphine antagonist in response to influxes of exogenous morphine-like substances, such as heroin, in default of addiction therapy.

The gel of the first and second aspects of the invention may be provided in combination with a semi-permeable or permeable membrane. Suitable membranes may be of the dialysis type, e.g. with molecular weight cutoffs of 10K-500K or may be microfiltration type membranes, e.g. with pore sizes of 0.025 to 0.1 µm which may be of cellulose or polycarbonate. The former membranes are preferred when the gel of the present invention is used as a sensor and the latter are preferred when the gel is used in a drug delivery system.

The gel-sol transition of the gel composition of the first and second aspects of the invention in response to raised levels of the analyte can be used to release a drug, preferably which acts to lower levels of the analyte. Thus, according to a third aspect of the invention, there is provided a drug delivery system comprising a gel composition in accordance with the first or second aspects of the invention and a drug, the drug being contained either (a) within the gel composition or (b) in a reservoir with the gel composition forming a barrier between the reservoir and the area to which the drug is to be released.

In the third aspect, "drug" is intended to mean any active agent, the delivery of which has a desired therapeutic or prophylactic effect.

As mentioned previously, the binding of the first and second gel-forming moieties, and hence the viscosity of the gel composition, is sensitive to the level of an analyte. This change in viscosity can be used to control the permeability of a solute within it. Thus, gel compositions of the present invention can form a closure to a reservoir or container containing a drug. Release of the drug from the container is governed by the viscosity of the gel, i.e. the level of the analyte. Alternatively, the drug can be contained within the gel itself. It is preferred if the gel composition is sensitive to glucose (e.g. a ConA/dextran-based gel) and the drug to be released is an anti-hyperglycaemic drug such as insulin. It is also possible for a glucose-sensitive gel to be used to control the release of any drug, the release of the drug being controlled by the administration of glucose to the patient.

When the drug delivery system of the present invention is used to deliver insulin, it is preferred if it is used intraperitoneally because this allows glucose to reach the system quickly and for insulin to be released quickly, than say if the system were used subcutaneously. In addition, peritoneal fluid has a glucose level which mirrors blood glucose levels. That is not to say that the system cannot be used subcutaneously or even externally—the location should be selected so as to suit the condition to be treated and the drug to be released.

According to another aspect of the invention, there is provided a sensor for detecting the level of an analyte, the sensor comprising a gel composition in accordance with the first or second aspect of the invention and means for detecting the viscosity of the gel.

The change in viscosity of the gel compositions of the present invention in response to altered levels of analyte means that they can be used to monitor analyte levels.

The viscosity of the gel may be detected in the manner described in DE-A-4203466, Ballerstadt & Schultz, *Sensors and Actuators B Chemical*, (1998), 46: 557-567, DE-A-4034565 or WO99/48419.

In order to be able to monitor changes in analyte levels in close to real time, the analyte must be able to diffuse easily through the gel composition and, when present, the membrane. As mentioned previously gel compositions of the present invention allow this without escape of the gel components. In order to increase response times further, it is desirable to detect the viscosity of a very thin (e.g. 4 mm or less, preferably 0.1-2 mm, although a monolayer is also contemplated within the invention) layer of gel. In such instances, it is particularly important to prevent loss of gel.

According to a further aspect of the invention, there is provided a method for the production of a gel composition of the first aspect of the invention, the method comprising:

causing first and/or second gel-forming moieties to become attached to cross-linked particulate entities, the first and second gel-forming moieties being capable of binding reversibly to one another to form a gel, wherein said binding is sensitive to the level of an analyte, and the interstices between the entities allow gel-sol and sol-gel transformation, and yet are not so small that the analyte cannot diffuse therethrough.

In a still further aspect, the invention provides a pharmaceutical composition for transdermal administration of an active agent, the composition comprising a carrier which either (a) contains the active agent or (b) forms a barrier between the active agent and the area to which the active agent is to be released, wherein at least a part of the carrier is digestible by one or more skin enzymes such that the active agent is released from the composition by the action of said enzymes.

The invention also provides (a) the use of such a composition in medicine, (b) the use of such a composition in the manufacture of a medicament for transdermal administration of an active agent, and (c) a method for administration of an active agent, comprising applying to the skin of a patient in need of such administration such a composition.

In this aspect of the invention, a therapeutic agent can be released variably but in a controlled manner: the intensity of medication is appropriate for the seriousness of the symptoms appertaining at the time, the trigger for increased release being a function of the skin condition. The composition is particularly useful for releasing a drug used in the treatment of skin diseases, particularly inflammatory skin diseases, which are known to be of an inconstant nature and have sequelae of under- and over-mediation using acknowledged drugs. For example, in the course of psoriasis, psoriatic stratum corneum may be more permeable when quiescent than in its thickened plaque state (Tang, et al. (1999). *Clin Pharmacokinet* 37(4): 273-87). Therefore, relying on healing to slow uptake in this case is not a useful mechanism for self-adjustment of dose in psoriasis. Thus, a control system based on output from the formulation comprising the drug is in general considered superior to one that relies on a physiological uptake mechanism.

The active agent is not covalently attached to the carrier, and the carrier merely acts to contain (i.e. the active agent is dispersed within the carrier) or restrain (i.e. the carrier forms a barrier to the release of the active agent) the active agent. This arrangement has the advantage that it is widely applicable to a number of potential drugs because it does not require any covalent modification of the active agent, however minor.

The carrier may comprise cross-linked particulate entities as defined above with a linear or possibly branched polymer bonded to them so that each entity has a fringe of polymer. The interstitial regions between the particulate entities are occupied by the polymer, providing a rheologically-active medium for drug diffusion. As discussed above, these regions have the ability to transport drugs through them relatively unhindered compared to gels made with homogeneously meshed linear polymers. The polymer affects the viscosity of these interstitial regions, reducing the diffusion coefficient of free drug compared with interstitial regions without polymer. The action of skin enzymes digest the polymer and thus raise the diffusion coefficient of the drug held in the formulation. Preferably, the polymer has vulnerable points at many places in its structure so that the long chain is broken into small fragments if the enzymes are present. Carbomer itself is quite resistant to enzyme activity and in its native state is actually protective towards proteins vulnerable to proteolysis (Hutton, et al. (1990). *Clin Sci (Colch)* 78(3): 265-71; Luessen, et al. (1995). *Pharm Res* 12(9): 1293-8; Walker, et al. (1999). *Pharm Res* 16(7): 1074-80). Its stability can maintain a minimum viscosity appropriate to a non-drip dermatological preparation, even when enzymes actively affect the polymer, but its protective effect lessened due to the modification of the surface.

Clearly, the selection of the polymer depends on the ability of skin enzymes to degrade it to release the active agent. Polymers or molecules which are degraded by one or more of the following skin enzymes can be selected by those skilled in the art: elastase (Chandler, et al. (1996). *Biochem Biophys Res Commun* 228(2): 421-9) which is a lysosomal proteinase responsible for the breakdown of elastin fibres in the ageing process, but also found in psoriasis; SCCE or stratum corneum chymotryptic enzyme (Ekholm & Egelrud (1999). *Arch Dermatol Res* 291(4): 195-200), a serine protease known to participate in surface cell shedding and to be implicated in psoriasis; and LTA4 hydrolase which can produce the abnormal leukotriene LTB4 from LTA4, a process also observed to occur in psoriasis. These three enzymes have esterase and/or amidase activities which are not necessarily specific for their original physiological substrates. It has been shown (Higuchi, et al. (1988). *Inflammation* 12(4): 311-34) that crusts formed in experimental lesions are rich sources of proteases and they have also been found in sweat (Horie, et al. (1986). *Am J Physiol*: R691-8). Furthermore, stratum corneum thiol protease (SCTP) is a cysteine protease recently found in the upper regions of stratum corneum. It is gelatinolytic as measured by zymography and functions best at the slightly acidic pH of the skin (Watkinson, (1999). *Arch Dermatol Res* 291(5): 260-8). Collagenases belong to the metalloprotease (MMP) enzymes which control collagen turnover in connective tissue, organ tissue, bones and cartilage among other locations. They are important in normal and abnormal skin including the healing of wounds (Simeon, et al. (1999). *J Invest Dermatol* 112(6): 957-64). A subset, type IV, the gelatinases MMP-2 and MMP-9 plus their specific inhibitors, are found in the dermis and epidermis, often associated with the keratinocytes and the Langerhans cells for which they modulate cell migration within the matrix during skin function (Kobayashi, Y. (1997). *Immunology* 90(4): 496-501; Makela, et al. (1999). *Exp Cell Res* 251(1): 67-78). The proteolytic activity is well understood (Seltzer, et al. (1990). *J Biol Chem* 265(33): 20409-13; Seltzer, et al. (1989). *J Biol Chem* 264(33): 19583-6) but the role in disease less so. There is some confusion in the technical literature about the detail but there are always raised levels of MMPs, m-RNA and their natural inhibitors in inflammatory skin diseases (Feliciani, et al. (1997). *Exp Dermatol* 6(6): 321-7; Buisson, et al. (2000). *J Invest Dermatol* 115(2): 213-8; Fleischmajer, et al. (2000). *J Invest Dermatol* 115(5): 771-7). Faults in the construction of the psoriatic dermal-epidermal have been attributed to the overexpression of the enzyme and the enzyme has also been found in keratinised layers near the surface. In psoriasis, gelatinase may be raised in those skin areas that are particularly involved.

Preferably, the polymer is selected from soluble synthetic homo- and co-polymers of amino acids (i.e. synthetic polypeptide analogues), mucin, collagen and gelatin. These all contain amine groups so that the attachment of polymer to the carbomer carboxylate groups can be accomplished using a standard carbodiimide method, but could also form Schiff base conjugates. Chitosan, a biodegradable polysaccharide may also be used.

Soluble synthetic homo- and co-polymers of amino acids need hydrophilic groups, such as pendant amines, hydroxyls and carboxylates, to have solubility. These compounds, such as e.g. polyaspartate and polyglutamate, can be viscous at high molecular weight. Some have previously been used in drug delivery (Singer, et al. (2000). *Ann N Y Acad Sci* 922(136): 136-50; Yi, et al. (2000). *Pharm Res* 17(3): 314-20) but are very expensive.

Mucin is a glycoprotein with a substantial viscosity and can be purchased (Sigma) in various degrees of purification: Type I (the purest with 12% bound sialic acid), type II and III (progressively more crude and each with 1% sialic acid).

Collagen and gelatin have a number of favourable characteristics, including a relevance to skin collagenases as discussed above. Collagen itself is expensive, and therefore it is currently preferred to use its cheaper derivative, gelatin.

Gelatin is a soluble proteinaceous derivative of collagen. It has well known rheological properties such that it is free flowing and viscous above a critical temperature (which in some grades is around 36° C.), and an elastic solid below this temperature, provided the concentration is high enough. It is not toxic and has been used in topical preparations, at least in experimental and development work as well as for buccal application, rectal use, dermal injections, as deep wound dressings and as an iv plasma expander. Some gelatin is of bovine origin and carries theoretical risks of prion contamination but there are alternative sources The World Health Organisation has dictated that pharmaceuticals containing gelatin should be made from supplies from BSE-free countries (WHO/EMC/DIS/96.147).

Like the parent collagen, gelatin contains seven main amino acids (plus several others in small percentage). The molecular arrangement is unusual because of the proline twist which promotes the formation of the triple helix structure in collagen. Four of the main amino acid residues contain hydrophilic pendants to which covalent attachments can be made. The availability of groups makes gelatin suitable for interstitial fringes as described above. Indeed, it can be bonded to a carbomer via the terminal amine groups in lysine and hydroxylysine and arginine residues. Gelatin is degraded by collagenases as well as a variety of other proteases, including some chymotrypsins and elastases. The liquefaction of a gelatin substrate is used to indicate chymotrypsins in stool tests for cystic fibrosis and for the identification of certain bacteria.

Active agents that can be used in this aspect of the invention for the treatment of psoriasis include:

salicylic acid, tars, dithranol (anthralin)

steroids, vitamin D analogues, retinoids (vitamin A analogues)

psoralens, methotrexate, ciclosporin (cyclosporin)

Steroids such as mometasone and fluticasone are often prescribed alone or in combination with retinoids such as tazarotene or with vitamin D analogue calcipotriol. Steroids, vitamin D analogues and more recently, retinoids, have been marketed for some years as straightforward topical applications such as ointments, creams and gels. Patients have a preference to these treatments over tars and dithranol because they are at least as effective and easy to use (Poyner, et al. (2000). *J Eur Acad Dermatol Venereol* 14(3): 153-8). The following will focus on the retinoids which may have particular appeal as discussed below, but this aspect of the present invention is all three of the above groups.

Retinoids form a group of compounds of which vitamin A compounds form a subgroup and have the biological activity typified by the alcohol retinol. Retinol (1) itself is metabolised reversibly to retinaldehyde (retinal) (2) and thence to the non-vitamin A but therapeutically active, retinoic acid (3)

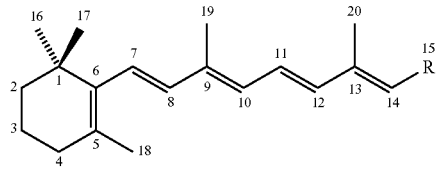

(1) R = $CH_2OH$        (6) R = $CH_2NH_2$
(2) R = CHO              (7) R = CH=NOH
(3) R = $CO_2H$          (8) R = $CH=N[CH_2]_4CHNH_2CO_2H$
(4) R = $CH_3$           (9) R = $CO_2C_2H_5$ (5) R = $CH_2OCOCH_3$

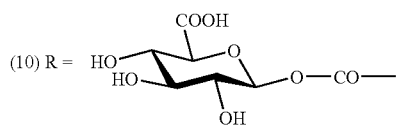

The retinoid nomenclature is often stretched to include other biologically related materials such as the arotinoids, of which the recently introduced agent tazarotene is a further modified analogue, used for treatment of psoriasis. Adapalene is pharmacologically similar but structurally distant.

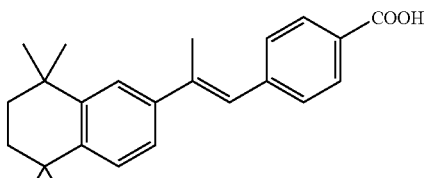

arotinioid structure

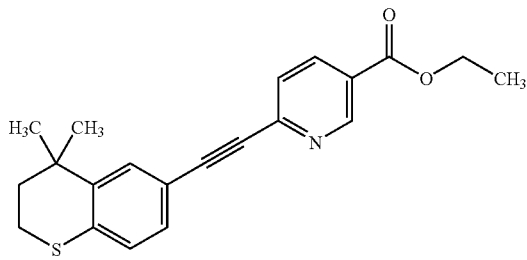

TAZAROTENE (EN: 145711)

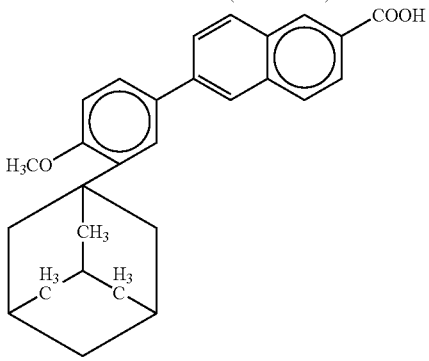

adapalene

The retinoids are important in the transmission of visual signals, and in the growth and differentiation of cells. The stereochemistry of these compounds importantly involves the polyprenoid side chain that can be all-trans or exhibit various cis isomerisations. Chiral centres also exist in the ring at the 1 and 3 positions. The stereochemistry is important for some of the biological activity of retinoids. In the mammalian retina, for example, the protein rhodopsin, is reversibly transformed by light as its aldehydic chromophore retinal converts between the all-trans and 11-cis forms.

In the skin, some retinoids, including retinoic acid isomers (Vahlquist, (1999). *Dermatology* 1(3): 3-11) and their relatives, activate particular nuclear receptor types in keratinocytes, some of which may be stereosensitive, triggering gene expression. This has at least three effects including the production of mRNA and protein pertinent to receptor induction, proliferation of epidermis and changes in the keratinisation processes (Didierjean, et al. (1999). *Exp Dermatol* 8(3): 199-203). The mechanism of action of these and related compounds in the treatment of psoriasis is, however, not clear (Saurat, (1999). *J Am Acad Dermatol: S*2-6) and the evidence is somewhat paradoxical. First, there is apparently no correlation between the observed binding to the receptors and therapeutic activity such that acetretin activates receptors without binding while tazarotene shows differential binding to three receptor subtypes. This may be a temporary confusion resulting from the variations within the three receptor subsets. The second puzzle is that lesions already show increased retinoic acid (isotretinoin) formation (Arechalde &

Saurat (2000). *Biodrugs* 13: 327-333), yet orally this compound and acitretin (an ester) work well and have been shown to control cell differentiation and sequential metaplastic changes. Recent work points to a decreased mRNA expression in lesional skin following receptor activation (Torma, et al. *Acta Derm Venereol* 80(1): 4-9), possibly partially explaining this finding. Oral isotretinoin and acitretin (a recent replacement for etretinate) have been used for more than two decades to treat psoriasis but involve a significant list of contraindications and precautions. The application of retinoic acid topically is used to treat acne and not listed in the BNF for antipsoriatic activity. However, the introduction of tazarotene (Tang, et al. (1999). *Clin Pharmacokinet* 37(4): 273-87) for this indication shows that it may feasible to use other retinoids topically for psoriasis, despite the receptor subset specificity claimed for tazarotene, which also has an excellent safety profile (Marks, R. (1998). *J Am Acad Dermatol:* S134-8). However, it is reported that new receptor subset-specific retinoids are under development possibly as an antidote to the mucocutaneous toxicity of oral isotretinoin (Nagpal & Chandraratna (2000). *Curr Pharm Des* 6(9): 919-31). Rosacea (Vienne, et al. (1999). *Dermatology* 1(53): 53-6) and photo-damage (Katsambas & Katoulis (1999). *Adv Exp Med Biol* 455(477): 477-82; Sorg, et al. (1999). *Dermatology* 1(13): 13-7) may also respond to topical retinoids, while retinoids delivered topically may protect skin against the atrophic effects of topical steroids (McMichael, et al. (1996). *Br J Dermatol* 135(1): 60-4). The applications extend as tazarotene is also used for acne, as is adapalene.

Locally applied retinoic acid is less toxic than oral retinoids but nevertheless produces irritation and erythema. However, use of the aldehydic prodrug retinal, has been reported as particularly attractive because it is less aggravating and exerts its effects by conversion within keratinocytes, to active species, after which receptor interaction occurs (Didierjean, et al. (1999). *Exp Dermatol* 8(3): 199-203; Sorg, et al. (1999). *Dermatology* 1(13): 13-7). Much is esterified and acts as a storage reservoir. The remainder is metabolised to small quantities of bioactive alcohol and acid forms. The latter occurs at a rate dependent on the oxidation capability of cells, which itself is related to the differentiation and thus possibly overt disease status of the cell population (Sorg, et al. (1999). *Dermatology* 1(13): 13-7). In terms of biological results, the all-trans retinal, which is metabolised to the all-trans retinoic acid (tretinoin) was found superior to a 9-cis analogue, which is likely to have formed the corresponding retinoic acid isomer (Didierjean, et al. (1999). *Exp Dermatol* 8(3): 199-203).

The retinoids are known to be teratogenic. Retinoids are ubiquitous signalling molecules and their deficiency and inappropriate availability both cause developmental faults. A variety of effects has been documented including craniofacial, limb and nervous system defects (Kubota, et al. (2000). *Eur J Pediatr Surg* 10(4): 248-51). The major risks may be for oral preparations but cannot be ignored for topicals, although tests with an animal model have used many times the topical concentration of isotretinoin without harm to the foetus.

The retinoids are in formulated products as follows:

| Tigason | (Roche) | etretinate | | Discontinued |
|---|---|---|---|---|
| Neotigason | (Roche) | acitretin | | 10 mg oral |
| Roaccutane | (Roche) | isotretinoin | (13-cis retinoic acid) | 5 mg oral |
| Isotrex | (Stiefel) | isotretinoin | | 0.05% gel (for acne) |
| Retin A | (Janssen Cilag) | tretinoin | (all-trans retinoic acid) | 0.01% gel (for acne) |
| | | | | 0.025% cream (for acne) |
| | | | | 0.025% lotion (for acne) |
| Retinova | (Janssen-Cilag) | | | 0.05% cream (for acne) |
| Zorac | (Bioglan) | Tazarotene | | 0.05% gel (for acne and psoriasis) 0.1% |
| Differin | (Galderma) | Adapalene | | 0.1% gel (for acne) |

The retinoids are very hydrophobic compounds. The water solubilities at room temperature and pH 7.3 buffer (with antioxidants) are documented as follows (Szuts & Harosi (1991). *Arch Biochem Biophys* 287(2): 297-304):

| retinol | 0.06 μM |
|---|---|
| retinal | 0.11 μM |
| retinoic acid | 0.21 μM | i.e. they lie between 0.000002 and 0.000006% w/v.

When used in this aspect of the invention, there must be sufficient water solubility of the drug to make it feasible to deliver an effective dose. The solubility figures above imply for example that the 0.01% w/v tretinoin gel in the list must contain a co-solvent. Retinoid preparations such as Isotrex and Acticin contain ethanol while others such as Differin contain propylene glycol and poloxomer, all in conjunction with gelling polymers such as hydroxypropylcellulose and carbomers. Alternatives are to formulate the gel with surfactants, such as the polysorbate 40 in Zorac and the technical literature shows complexation of retinoic acid with cyclodextrin for iv administration and other uses (Botella, et al. (1996). *Journal Of Pharmaceutical And Biomedical Analysis* 14: 909-915; Lin, et al. (2000). *J Clin Pharm Ther* 25(4): 265-9). A liposomal or similar lipid aggregate component could also function in a gel to increase the colloidally dispersed concentration (Li, et al. (1999). *Photochemistry And Photobiology* 69: 500-504).

Thus, in accordance with one embodiment of this aspect of the invention, a carbomer-gelatin conjugate can be used to deliver a retinoid in a skin enzyme-dependent manner. The retinoid may be conventional tretinoin, tazarotene or retinal, which is an inactive prodrug converted in situ. All of these have low solubility but may be solubilised in cosolvents, surfactants or liposomes.

Retinal and retinoic acids (isotretinoin and tretinoin) have groups which allow their conversion to conjugates. This can not only increase their water solubility but provide an enzyme-dependent release which could be used per se or alternatively in tandem with a pharmaceutical composition for transdermal administration of an active agent as described above.

In a still further aspect of the invention, there is provided a composition comprising a carrier which is covalently bonded to an active agent, wherein the bond between the carrier and the active agent is digestible by one or more skin enzymes, for use in medicine, in particular for transdermal administration of the active agent.

The invention also provides a method for administration of an active agent, comprising applying to the skin of a patient in need of such administration a composition comprising a carrier which is covalently bonded to an active agent, wherein the bond between the carrier and the active agent is digestible by one or more skin enzymes In this aspect of the invention, the active agent is covalently bonded (directly or indirectly) to the carrier. Enzymes making contact and mixing with the composition must be capable of cleaving this agent-carrier conjugate to release the medication. The conjugates can be considered to be prodrugs that undergo activating metabolism outside rather than inside the skin. The carrier could be one of a variety of polymers currently used in dermatological formulation, and it is preferable that the composition is single phase and aqueous. Polymers such as carbomer, polyvinylpyrrolidone or cellulose derivative, for example, with linear or more involved construction dissolve in an aqueous medium to give suitable properties. The connection between the drug and polymer may be direct or indirect. In the latter case, the connection may be via a bridging molecule. This molecule may also be polymeric in which case enzymes can release the drug by attacking bonds in the bridge. The molecule may be a peptide or polypeptide. Polymer bridges can be used to introduce enzyme specificity in conjugates used systemically. In either case, many drug molecules can be attached to various parts of the polymer structures, provided of course that the drug is undamaged by the conjugation and cleavage.

Such conjugates are known but do not appear to have been used for transdermal administration before. Schiffs base conjugates with retinal have been studied in an attempt to elucidate how rhodopsin operates as an optically-activated neurotransmitter. Thus, retinal conjugated with dextran, polylysine, polyethylene glycol have been described as water soluble conjugates, while Schiff base conjugates of retinal with phosphatidylethanolamine and with alkylamines produced micellised aggregates (De Pont, et al. (1969). *Exp Eye Res* 8(2): 250-1; Adams, et al. (1974). *Exp Eye Res* 18(1): 13-7; Pitha, et al. (1980). *J Natl Cancer Inst* 65(5): 1011-5; Freedman, et al. (1986). *Photochem Photobiol* 43(3): 291-5; Singh, et al. (1990). *Biochim Biophys Acta* 1036(1): 34-40; Viguera, et al. (1990). *J Biol Chem* 265(5): 2527-32). Such conjugates could therefore confer useful water solubility.

Preferred features of this aspect of the invention are as for the pharmaceutical composition for transdermal administration of an active agent described above.

Preferred features of each aspect of the invention are as for each of the other aspects mutatis mutandis. The prior art documents mentioned herein are incorporated to the fullest extent permitted by law.

The invention will now be described further in the following non-limiting examples.

EXAMPLES

Introduction

Formulations of concanavalin A (con A) and dextran have been shown previously to be glucose sensitive. Con A is a protein with a glucose receptor in each of the subunits contributing to the structure. The protein is dimeric below pH 5.8 but tetrameric between pH 5.8 and 7.0, above which point it begins to form larger aggregates. The receptors accommodate free glucose but also terminal glucose units on polysaccharides such as dextran. Because dextran is multivalent in its complement of such terminals, an admixture with the lectin produces complex structures which can be either a precipitate or gelatinous. The structures are destabilised by the addition of free glucose which competes for occupation of the receptor sites. Under circumstances where glucose is added to a gelatinous formulation of the mixture, the viscosity falls sharply but is regained if glucose is dialysed out. This mechanism forms the basis of a delivery device for hypoglycaemic agents such as insulin which would diffuse more slowly through the gel if ambient glucose levels were low but could be triggered into a higher delivery rate if the viscosity was reduced by contact with glucose.

A problem with this design is the tendency of the components to leach away from the gel. The components are water dispersible when the gel becomes dismantled and some means is required by which the sol form is stabilised to prevent loss from the formulation but which will not prevent the viscosity change upon which the design depends. In the following, the lectin was exposed to a procedure to bond it covalently to commercially-produced carbomer types Carbopol 974 and 934 (referred to as C974 and C934). These materials are polyacrylic acid derivatives which have been three-dimensionally cross-linked to produce gelatinous, but particulate, entities, each with a molecular weight of several billion. The bonding has been done with 1-ethyl-3-(3-dimethylaminopropyl) carbodiimide hydrochloride (EDAC), which operates to give a temporary intermediate structure between the EDAC and a carboxyl moiety (in this case from the carbomer sites (see FIG. 6)). The intermediate can then bond with amine groups, such as are found in proteins including con A at terminal and lysine sites. This results in the formation of an amide linkage and the loss of the EDAC residue. The con A can become effectively conjugated with the carbomer such that the surface of the carbomer particles becomes permanently coated with lectin.

The carbomers C934 and C974 differ from many polymeric gels in that, although they are both cross-linked, neither is an integral structure. Each hydrated particle is in effect a discrete hydrogel and interstitial aqueous regions separate it from neighbouring particles. This means that large molecules like insulin can diffuse through a carbomer gel of this type more rapidly (FIG. 7*a*) than through gels made from linear polymers (including linear carbomer types) or through regular hydrogels. In both the latter, the obstructions are greater since physical and chemical entanglements respectively occur throughout the structures and could well be rate-determining for insulin transport.

Reagents

Carbopol 974 (C974), Carbopol 934 (C934) BF Goodrich

EDAC [1-ethyl-3-(3-dimethylaminopropyl)carbodiimide hydrochloride], Sigma

MES [2-(N-morpholino)ethanesulfonic acid], Sigma

PBS (phosphate buffered saline, pH 7.4 & 5.9)

NaOH (pellets and 1M solution), Fisher Scientific dextran (RMM 2 000 000), Sigma sodium azide, Sigma concanavalin A, Sigma distilled water
1M HCl (hydrochloric acid), BDH

Example 1

Production of Gel and Measurement of Viscosity

A 1% w/w carbomer dispersion was made in 0.1M MES buffer, adjusted to neutral and stirred until clear. Con A was then added to this such that the final concentration was also approximately 1% w/w and the pH kept at neutral. The system was then conjugated using 50 mM EDAC, the reaction being quenched after stirring for three hours at room temperature by diluting with PBS at pH 5.9 and centrifuging washings from the partially-dehydrated carbomer conjugate until washings revealed no further con A in the supernatant. The total protein removed was calculated by assaying bulked and filtered washings at 276 nm. The coupling efficiency was greater than 90%. A 1 g quantity of a 20% w/w dextran D2M (mw 2 million) solution in PBS (pH 7.4, preserved with 0.01% sodium azide) was then added to the neutralised carbomer-con A conjugate and mixed thoroughly. The final product therefore contains 200 mg each of carbomer and dextran D2M. The pH of the gel was then adjusted to 7.4 using 1M NaOH and a stiff, glucose responsive gel results. The final weight is slightly variable, depending on the final pH adjustments and the contents are calculated accordingly.

Both C974 and C934 were conjugated in this way and subjected to viscosity testing in the presence of varying concentrations of glucose. The viscosity measurements were obtained using a Haake Rheostress RS75 cone and plate viscometer in continuous rotation mode where rate of shear was ramped between 0 and 5 s$^{-1}$. The viscosity values corresponding to a shear rate value of 5 s$^{-1}$ were used to compare the gels at the glucose concentrations between 0 and 5% w/v. The gels were compared at 20° C. and the C934 product was also measured at 37° C.

The conjugates produced from the particulate carbomers, C974 and C934, were calculated to have compositions as follows:

|  | C934 (formula code E100) | C974 (formula code E87-5) |
| --- | --- | --- |
| Carbomer | 2.6% w/w | 2.7% w/w |
| Dextran D2M | 2.6% w/w | 2.7% w/w |
| Con A | 2.4% w/w | 2.5% w/w |

The formulations were rather opaque in comparison with the extreme clarity of carbomer gels from which they are derived. The protocol in which the con A was added in the presence of excess EDAC is likely to have produced a variety of products which might include strings of lectin added to the carbomer. This is because con A also has carboxyl groups which are vulnerable to the action of EDAC. However, this method gave a result in which the con A was bonded in high proportion and it was used in preference, at this stage, to one in which the carbomer-EDAC reaction was quenched prior to adding the con A.

In terms of assessing the performance of the formulations, it is useful to compare these products with simple aqueous combinations of dextran 2DM and con A without carbomer. However, a direct analogy was not possible, because 2.5% con A forms only precipitates with low concentrations of dextran in carbomer free aqueous admixtures. Accordingly, 2.5% con A was combined with 10% w/w D2M to form a low viscosity gel. This concentration of dextran in the presence of carbomer gave too viscous a product to be useful in the study and the dextran content in them is about 3% w/w.

Figure 8:
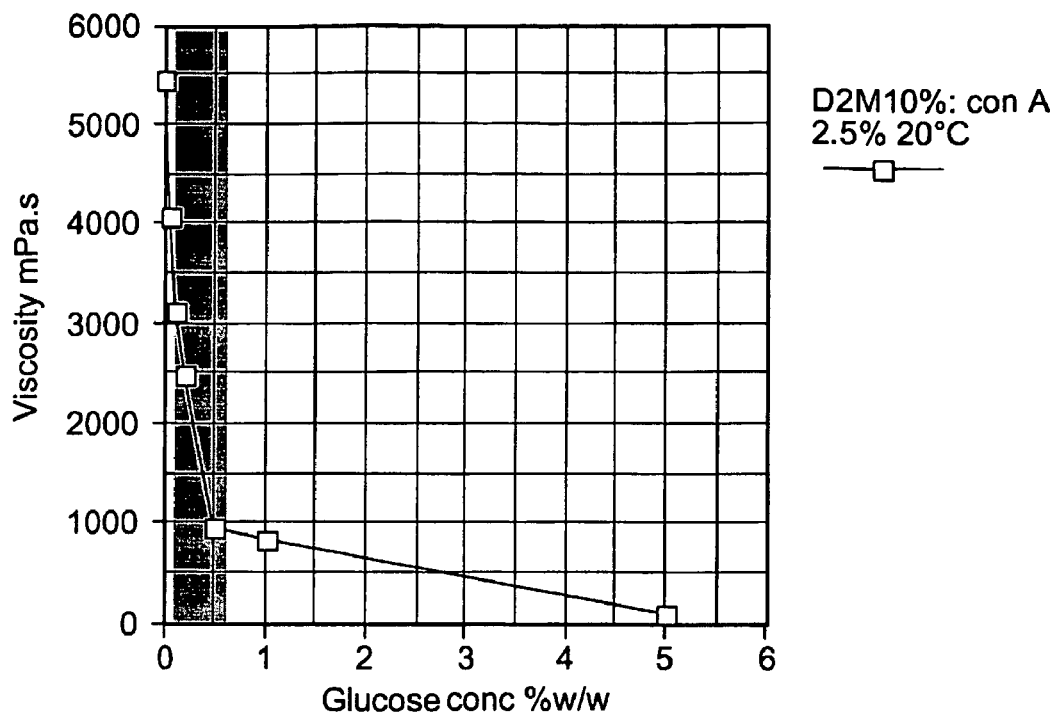
FIG. 8 is a graph illustrating that addition of glucose to an aqueous gel formulated with dextran and con A leads to a loss in viscosity.

FIG. 8 shows that the addition of glucose produces a progressive drop in the viscosity of the aqueous formulation mainly over the glucose concentrations 0-0.5% w/w (highlighted on the graph), which is a range relevant for the design of products useful in the control of diabetes mellitus. The response is dependent on the stoichiometry of the displacement mechanism described above and is therefore a function of the relative concentrations of dextran and glucose. It is this response which it is important to conserve.

Figure 9:
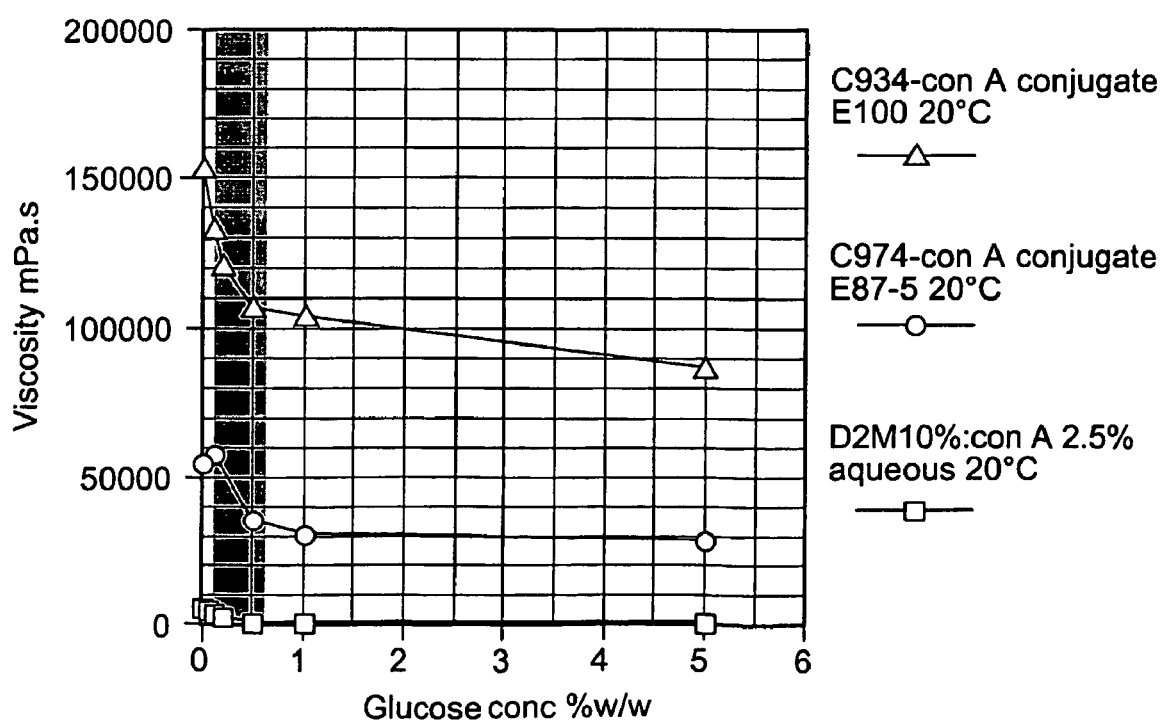
FIG. 9 is a graph showing that the addition of glucose to carbomer-containing gels formulated with dextran and con A leads to a loss in viscosity in the same range of glucose concentrations as an aqueous formulation.

The results in FIG. 9 show a drop in viscosity over a similar glucose range to the aqueous formulation, demonstrating that glucose sensitivity has been imposed on the carbomer particles. However, the baseline viscosity levels, at which the lectin-dextran linkages have been reversed with glucose, are much higher when carbomer is present because of the viscosity of this polymer.

FIG. 9 also indicates that the addition of dextran and con A has raised the viscosity of the glucose-free product by a much greater amount in carbomer systems than in plain aqueous ones, despite the lower dextran content used in the carbomer-containing formulations. This means that the glucose response, in terms of the viscosity change, is of a greater magnitude in the carbomer formulations than in the aqueous one, as is also shown in FIG. 9. This also happens to be the case if there is no covalent bonding of the lectin to the carbomer (not shown) and is therefore a function of the presence of the carbomer on the dextran-con A system. An explanation for this relates to the heterogeneity of the carbomer dispersion discussed above. The dextran and con A are restricted to the interstices because their size (mw 2 million and 100,000 respectively) must exclude them from C974 and C934 particle interiors. Their localised concentrations must therefore be much higher than the total concentrations because the interstices form a fraction of the total volume. This explains the difference in the physical properties of the complex formed between dextran and con A at the very low concentrations used in carbomer systems compared with entirely aqueous systems, as described earlier. In the carbomer systems, the microviscosity of the interstitial region clearly contributes much to the glucose sensitivity of the formulation. However, the macroviscosity changes caused by glucose, as sensed in this experiment, do not appear to be simply an average for an active interstitial and an inert particulate compartment because the glucose-induced changes are so much larger than in the homogeneous aqueous system. This seems to imply that the interstitial viscosity is not the sole reason for the increased glucose sensitivity of this system but probably that its presence influences the freedom of movement of the particles in the gel as a whole and thus has an additional effect on its macroviscosity.

Figure 10:
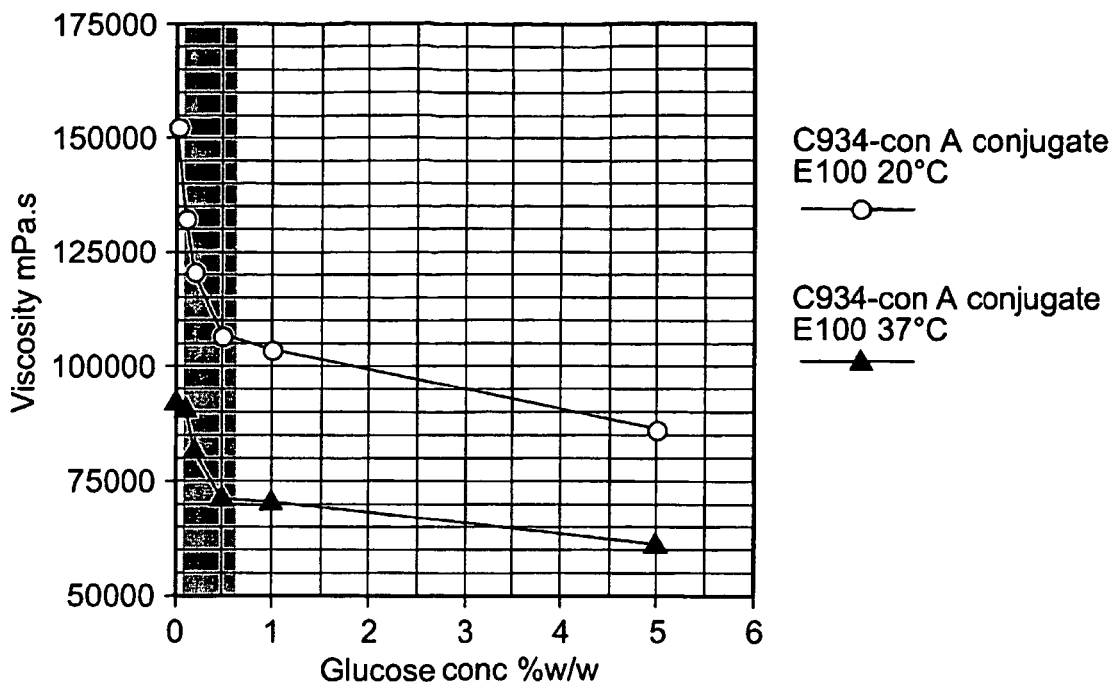
FIG. 10 is a graph showing that the addition of glucose to a carbomer-containing gel formulated with dextran and con A leads to a loss in viscosity at both 20° C. and 37° C.

A similar viscosity fall occurs at 37° C., as shown in FIG. 10 for the C934 conjugate. The viscosity values and the changes at 37° C. are both lower than for 20° C. as might be anticipated from the similar behaviours of both carbomers and the aqueous, carbomer-free formulations of dextran and con A (neither shown). However, the system is clearly a sensitive glucose sensor at physiological temperature.

Figure 11:
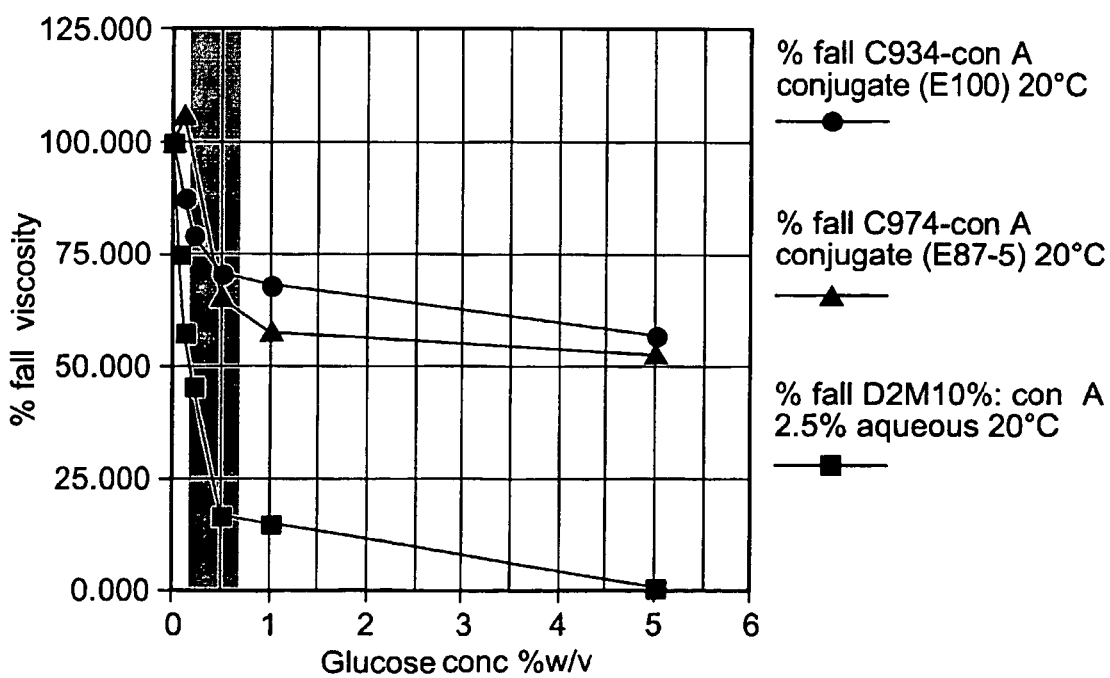
FIG. 11 is a graph illustrating the viscosity reduction on addition of glucose for carbomer-containing gels formulated with dextran and con A, and an aqueous gel formulated with dextran and con A, shown as a percentage of the original viscosity.

In the systems examined at 20° C., the viscosity change when expressed as a fraction of the original value is lower for the carbomer systems than for the aqueous systems, as is shown in FIG. 11, despite the higher absolute values.

The main reason for wishing to covalently bond the lectin to the carbomer is to prevent its escape from the formulation without sacrificing activity. The viscosity changes induced by glucose show that, after washing the carbomer several times by centrifuging the supernatant from it, it has glucose sensitivity. This suggests that the lectin has been successfully anchored to the carbomer particle surface using EDAC as the bonding agent. A plain mixture of carbomer and the lectin does not retain activity when washed in this way (not shown).

Example 2

Insulin Diffusion

The gels described in Example 1 were also subjected to insulin diffusion tests at 37° C. In these experiments, six small delivery cells were used, each capable of holding 0.5 mL of insulin solution or a buffer control solution. They were each mounted empty into temperature regulated receptor vessels, holding 10 mL of buffer and were connected by individual flow through systems to a Perkin Elmer Lambda 40 spectrophotometer, programmed sequentially to scan each receptor solution between 250 and 500 nm at ten minute intervals. The cells were filled by syringe at the required time and then sealed using a tap arrangement to make them watertight. In each cell, a thin layer of the gel was sandwiched between two filter membranes such that the insulin diffused through the gel from the reservoir in order to reach the receptor solution. Glucose could be added to individual receptor solutions in the concentration required at any time during the experiment. To remove the glucose, the receptor fluid was replaced between readings with new buffer at 37° C., the flow through circuit flushed and the buffer replaced again before the next reading was due.

Figure 12:
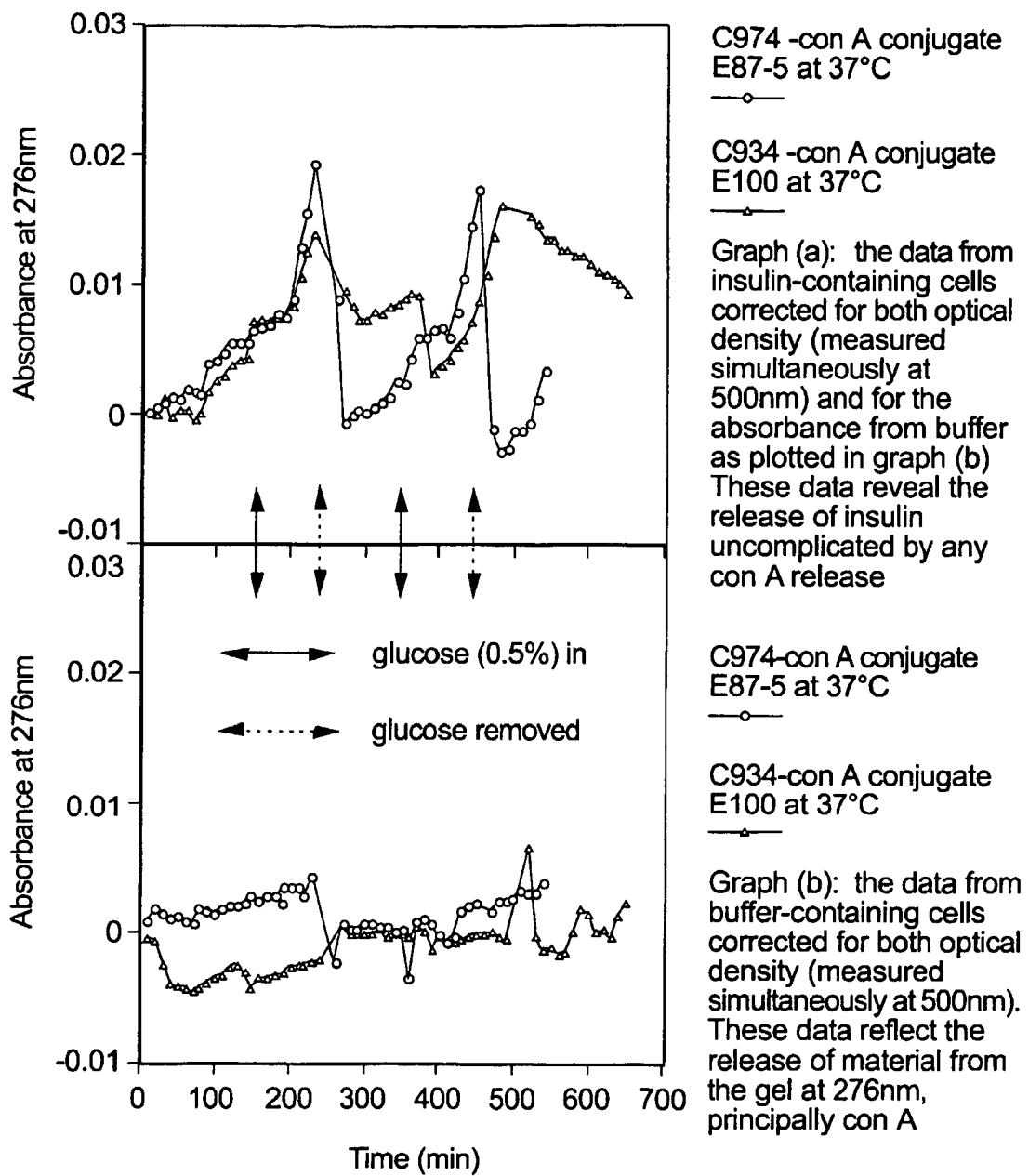
FIGS. 12a and 12b are graphs which illustrate the release of protein from a gel in accordance with the present invention.

For those diffusion cells containing insulin, the addition of glucose at the points shown on FIG. 12a has resulted in increased output within about 60 minutes of the addition of 0.5% glucose. FIG. 12b shows the results from buffer-containing control cells and represents the glucose provoked release of con A. This indicates that the con A loss from the gel layer has been minimised because, in aqueous dispersions, glucose-induced liberation similar to that of the insulin would have occurred (not shown). Although the loss of con A has therefore been shown to be almost negligible, the results in FIG. 12a have nevertheless been corrected for this effect. In addition, a correction has been made in both the insulin and the control systems, for optical density as measured at 460 nm. The optical density is a measure of protein precipitation, including the production of fibrils. Fibrillation is a much greater problem with insulin than with con A in this experiment. It results from the application of shear forces such as would be experienced by solutions circulating through a peristaltic pump. The flow rate in the circulation system from the receptor to the spectrophotometer was kept as low as possible in this experiment to reduce the problem, consistent with maintaining the release process from the device as the rate-determining process. The effect needs to be compensated for by subtraction from the 276 nm profile, however, because it does not remain a constant throughout the experiment as the glucose is removed by fluid replacement and because it is a non-constant function of protein concentration.

The result of covalent bonding of the lectin to the carbomers C934 and C974 and its combination with dextran has therefore maintained the activity of the glucose-dependent mixture of dextran and con A in terms of controlling the diffusion of insulin as a function of glucose content. This has operated at a concentration of glucose that represents a fairly severely diabetic state. The method has also has created a formulation from which con A cannot leach through apertures smaller than that which retains carbomers in the gel layer. Since carbomers like C934 and C974 have molecular weights in billions (and a particle size in the micrometer range), this effectively allows the use of very large pore restraining membranes in the set-up described in this example. The advantage of this is that the gel itself—and not the cellulose membranes between which the gel is sandwiched—will be rate-determining for the insulin. This has been a problem in unconjugated mixtures which require pore membranes with a molecular cut-off close to the size of insulin in order to retain the lectin.

The data presented in Examples 1 and 2 indicate that it is possible to produce unusual conjugates between particulate carbomers, such as C974 or C934, and a second component, such as a protein, in which some of the chemical characteristics of the protein can be preserved. In this case, con A has been bonded to cross-linked carbomers to produce systems in which the interstitial regions of the formulations become glucose sensitive. The EDAC method has been used but alternatives are possible. If dextran is added to this conjugate, the system becomes viscous because of the temporary links formed between the lectin and the branch ends on the dextran. The viscosity of this system is then a function of the free glucose content because of the competition for the glucose receptors in the lectin. This mechanism works well in the simple mixtures of con A and dextran but operates in an enhanced way in the covalently-conjugated formulation. This enhancement appears to be related to the heterogeneous structure of particulate carbomer gels in which the lectin-dextran complexes are formed in that fraction of the system between particles, creating high localised concentrations of the glucose-sensitive components. These conjugated formulations have been shown to produce glucose dependent reductions in macroviscosity. They have also have been able to transmit insulin in a glucose-related manner without the loss of free lectin. The latter remains covalently bound to the carbomer particles and therefore restrained by membrane pore sizes that need be small enough only to retain the carbomer particles, thus not compromising the rate-determining process in this glucose dependent transport system.

Example 3

Copolymerised Gels

Methods
Concanavalin A Methacrylation

Concanavalin A was refluxed at 50° C. for 2-3 hours with methacrylic anhydride in phosphate buffered saline at 7.4. 500 mg of ConA was dissolved in 10 mL phosphate buffered saline in a 50 mL round bottomed flask and to it was added 0.05 mL distilled methacrylic anhydride. After refluxing, the reaction was quenched with distilled water (20 mL) and the whole solution dialysed against distilled water for 2 days to remove products of mw<12-14,000. This process cannot remove unbonded con A.

Dextran Methacrylation

A 10 g quantity of D500, dextran of mw 500,000, was weighed and dried over phosphorus pentoxide. Separately dimethylesulphoxide (DMSO) was dried over calcium hydride and then distilled. A 100 mL quantity of distilled DMSO was then added to the dried dextran and the resulting mixture stirred to dissolve at 50° C. over an oil bath. To this was added 200 mg of dimethylaminopyridine (DMAP) and 2.77 mL of distilled methacrylic anhydride. The mixture was then stirred at 50° C. on the oil bath for 24 hours under reflux. Precipitation was achieved by adding dropwise into IL acetone to give white flakes of dextran methacrylate. The product was then dissolved in 500 mL of distilled water and dialysed against distilled water to remove small mw products such as DMSO, DMAP, methacrylic anhydride.

uv Cross-Linking of the Methacrylated Deriatives

An initiator, Irgacure (photoinitiator, Ciba Speciality Chemicals), was used to start a uv curing process. 20 µL of a 40 mg/5 mL aqueous solution of Irgacure was added. The sample was then irradiated at 365 nm at 10 mWatts/cm² for a predetermined time, split for equal irradiation of both sides of a spaced film between glass plates.

The variables in the system are:
concentration of components
concentration of initiator
degree of dextran and con A substitutions
irradiation time These variables allow gels of a wide variety to be made. In the following case, the irradiation time was varied between 2 and 50 minutes.

Diffusion Tests

The gels made as described above were then subjected to the same diffusion tests as referred to Example 2 and the results were as follows:

Results

Figure 13A:
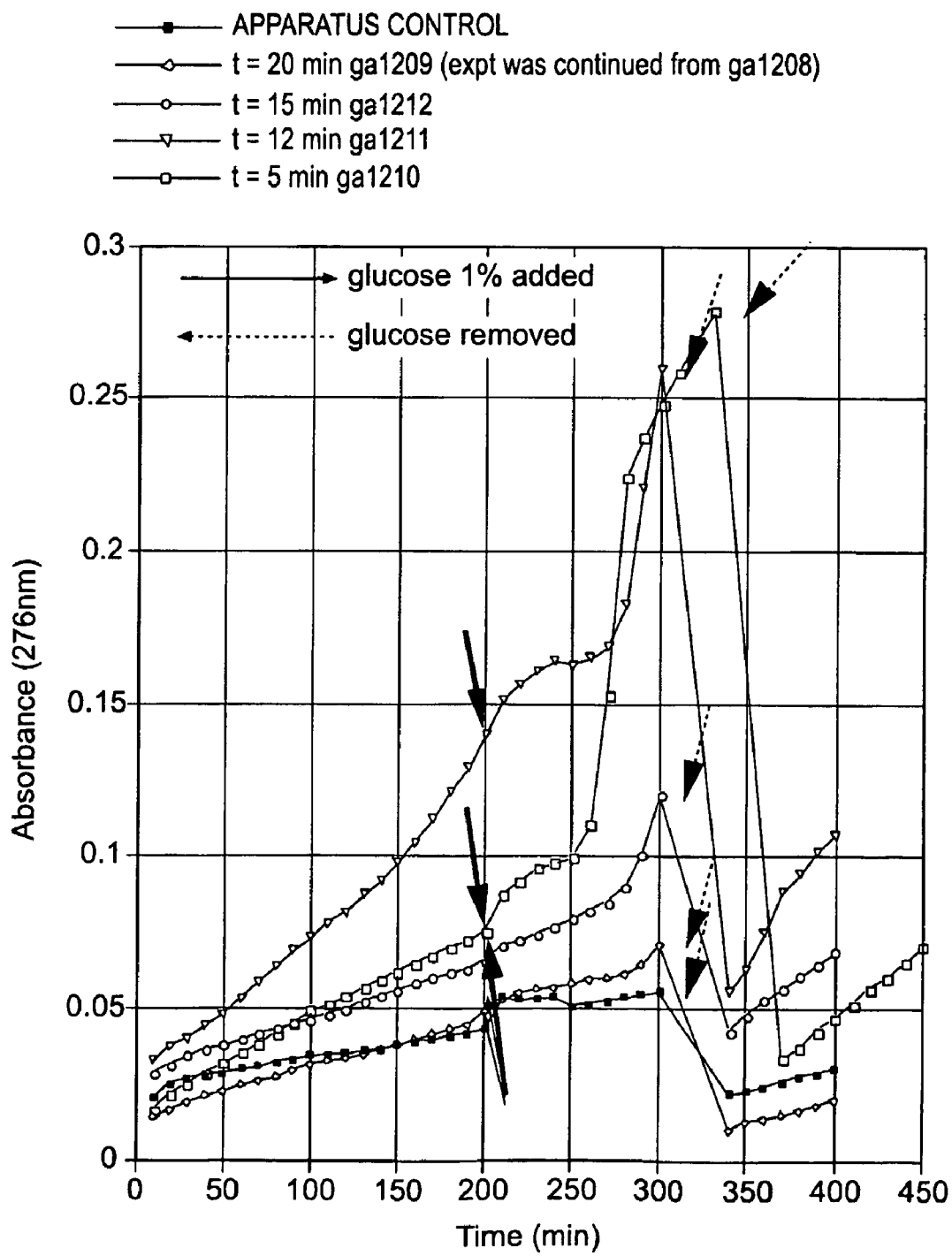
FIGS. 13a and 13b are graphs illustrating release of ConA from polymerable methacrylated derivatives of ConA having been subjected to varying degrees of polymerisation.

In FIG. 13a, the leach from polymerable methacrylated derivatives of the protein con A is plotted before and after the provocation with glucose (experiment conducted at 37° C., using 0.2 µm pore size filters, and glucose trigger concentration of 1% w/v). The increase in radiation time of a gel subjected to uv and an appropriate initiator, leads to a reduction in the peak of protein produced as the gel softens on contact with glucose. Short irradiation times (e.g. 5 min— triangle symbles) do not achieve this, whereas the 20 minute cure time (diamond symbols) produces only a slight leach. The polymerisation has therefore achieved the aim of locking in the protein within these longer-irradiated but still non-rigid gels. However, the comparison with the gel-free control (filled square symbols) shows that some protein release occurs throughout, albeit slight, even with 20 minute irradiation.

Figure 13B:
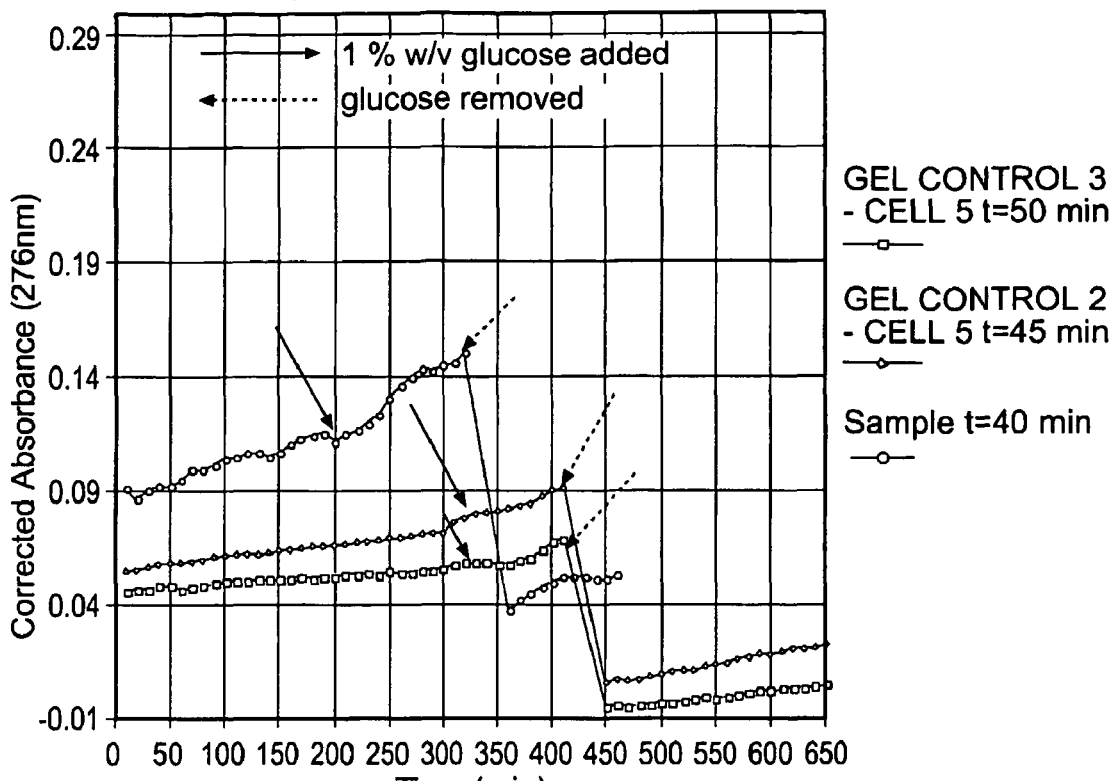

FIG. 13b shows that much longer irradiation times solve this problem and 50 minutes seems to give a product that hardly loses protein at all, either before, during or after glucose addition. This is also non-rigid and thus suitable for the purpose.

Figure 14:
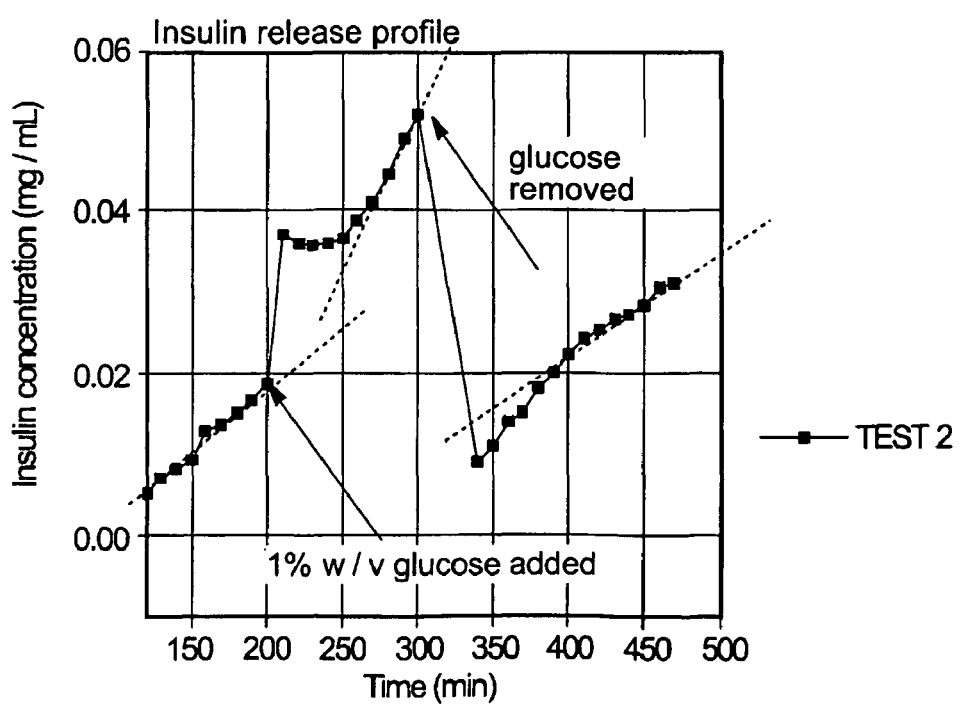
FIG. 14 is a graph illustrating insulin release by a copolymerised gel according to the present invention in the presence or absence of glucose.
Figure 15A:
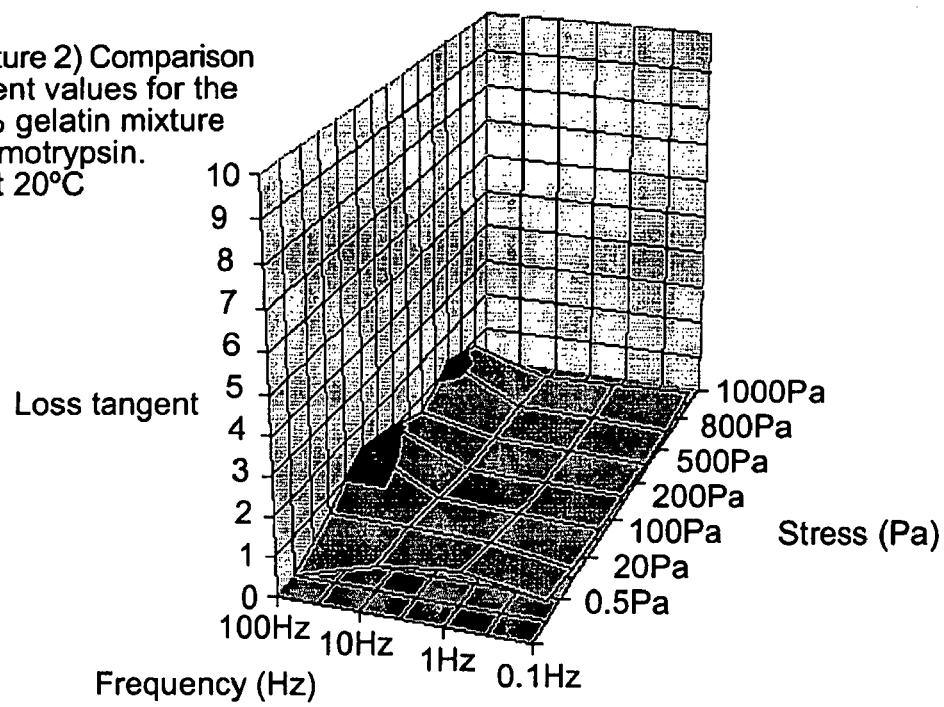
FIGS. 15a-c are graphs illustrating the loss of tangent values for a composition of the present invention in the absence of chymotrypsin at 20° C., 32° C. and 37° C. respectively.
Figure 15B:
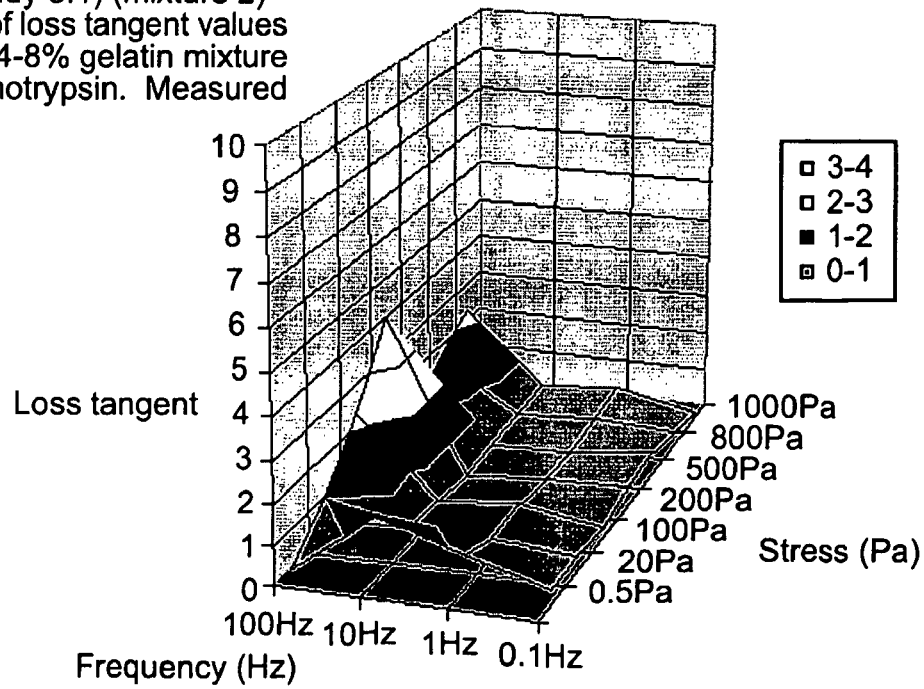
Figure 15C:
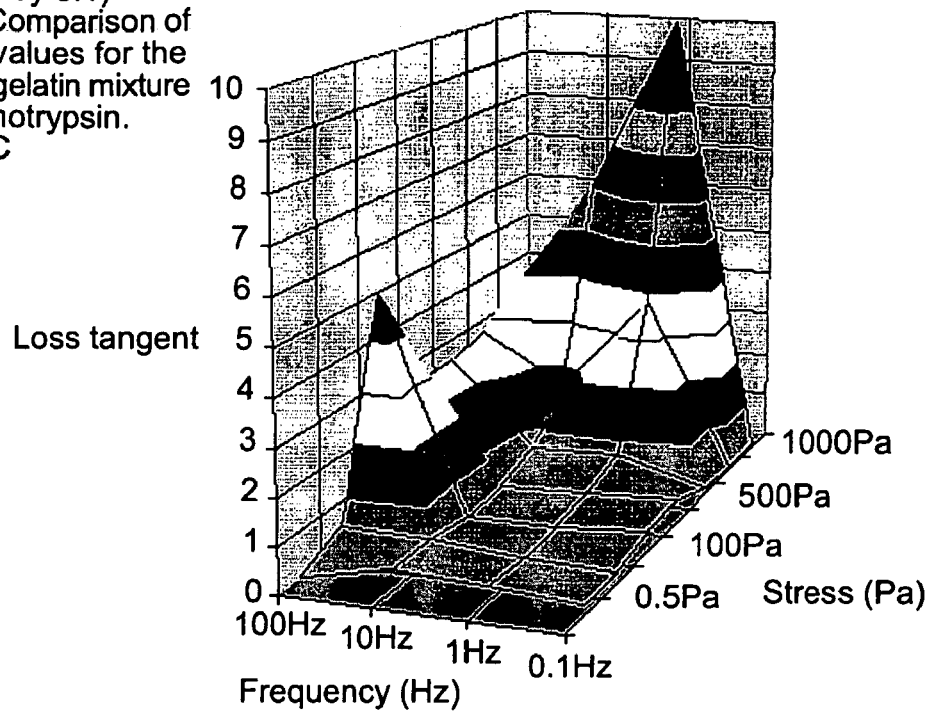
Figure 15D:
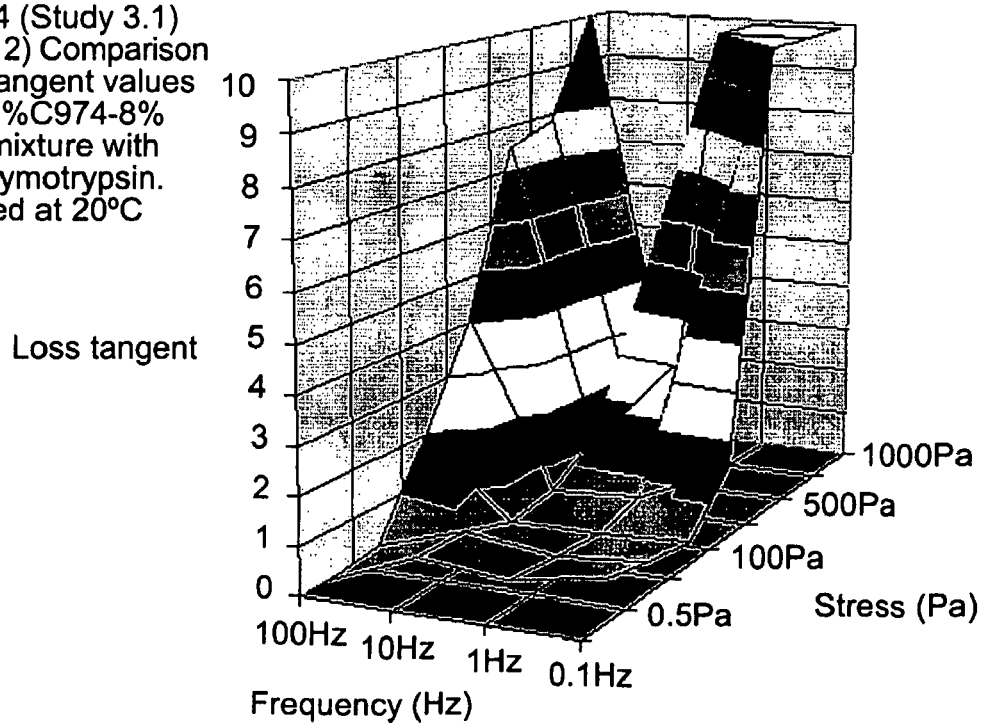
FIGS. 15d-f are graphs illustrating the loss of tangent values for the composition in the presence of chymotrypsin at 20° C., 32° C. and 37° C. respectively.
Figure 15E:
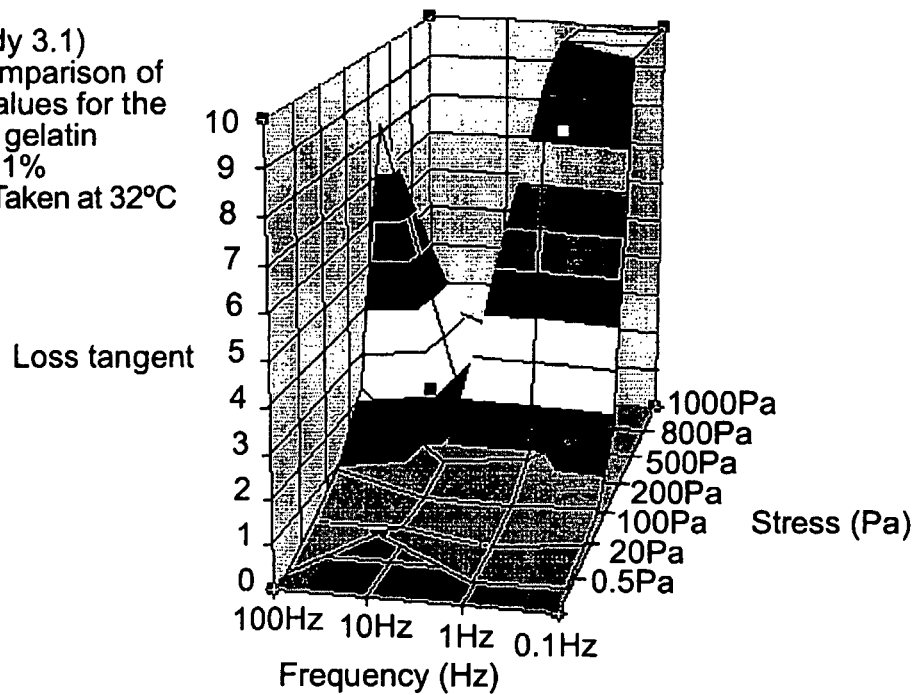
Figure 15F:
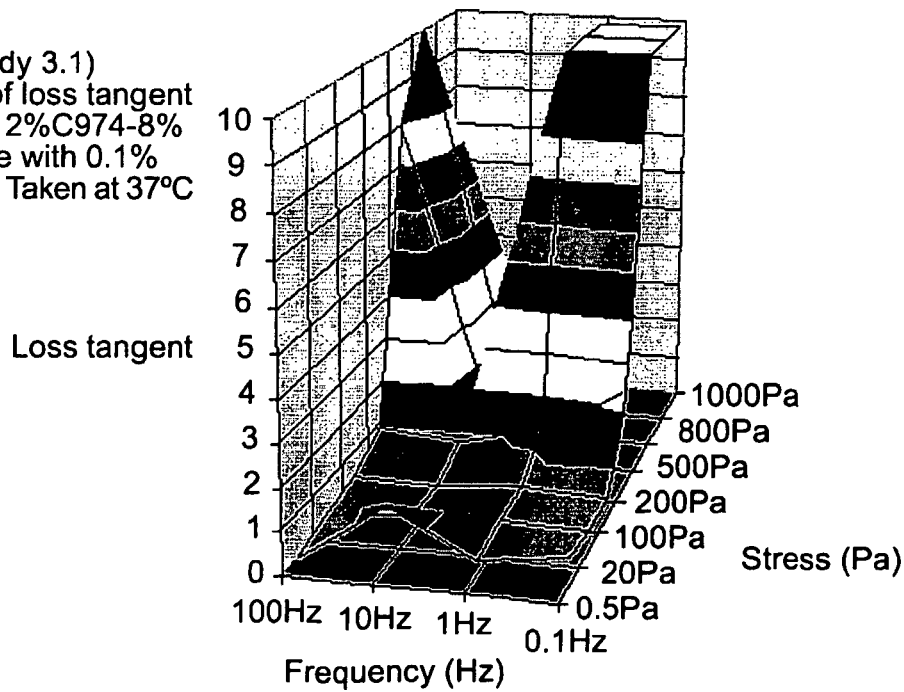

FIG. 14 indicates that under these conditions of minimised component leach, glucose can be shown to provoke a release of insulin from a reservoir held behind a layer of gel in an exactly analogous set up. The gel is therefore capable of response, such that insulin is released, but it will not leach out the component protein con A. The gel seems to reform after glucose removal, so that the insulin flux is restored to pre-glucose levels. This means it is truly reversible, implying that neither gel component is lost.

Conclusion

Polymerisation is an effective method for producing gels that are as responsive as the plain mixtures but resist the tendency to lose components.

Example 4

Gelatin:Carbomer Conjugation with EDAC

Conjugation between gelatin and carbomer has been done with 1-ethyl-3-(3-dimethylaminopropyl) carbodiimide hydrochloride (EDAC), which gives a temporary intermediate structure between the EDAC and the carbomer carboxyl moiety. The intermediate bonds with amine groups, such as are found in gelatin at terminal and hydroxylysine sites, among others. The gelatin is effectively conjugated with the carbomer such that the surface of the carbomer particles becomes permanently coated with gelatin while the EDAC residue leaves the permanent bond site. The method here fosters some gelatin-gelatin bonding in addition to carbomer-gelatin bonding since carboxyls and amines both occur in gelatin. This is of no disadvantage since it means that all gelatin added, even to quite high concentrations is likely to be bonded, even distantly, to the carbomer carrier, which therefore may have not simply monolayers but multilayers of gelatin bonded to each micro- (or mini-) gel hydrated carbomer particle.

However, the method can be modified to produce the intermediate (between the carbomer and EDAC), wash to remove excess EDAC and then bond gelatin, in which case, the gelatin content will be minimised (monolayer only).

Each hydrated carbomer 974 or 934 particle is a discrete hydrogel and separated from others by interstitial aqueous regions. This means that the gelatin bonded to the surface can raise the viscosity of the interstices until hydrolysed by enzyme or chemical action.

Reagents

Carbopol 974 (C974), Carbopol 934 (C934) BF Goodrich
EDAC [1-ethyl-3-(3-dimethylaminopropyl) carbodiimide hydrochloride], Sigma
MES [2-(N-morpholino) ethanesulfonic acid], Sigma
PBS (phosphate buffered saline, pH 7.4 & 5.9)
NaOH (pellets and 1M solution), Fisher Scientific
sodium azide, Sigma
gelatin, Sigma
distilled water
1M HCl (hydrochloric acid), BDH Method A 1% w/w carbomer dispersion was made in 0.1M MES buffer, adjusted to neutral and stirred until clear. Gelatin was then added to this such that the final concentration was between 0 and 8% w/w, depending on the desired product and the pH kept at neutral. The system was then conjugated using 50 mM EDAC, the reaction being quenched after stirring for three hours at room temperature by diluting with PBS at pH 5.9 and centrifuging washings from the partially-dehydrated carbomer conjugate until washings revealed no further con A in the supernatant. The total protein removed was calculated by assaying bulked and filtered washings at 276 nm. The pH of the gel was then adjusted to 7.4 using 1M NaOH and a stiffened gel results than responds to temperatures above 37° C. by softening significantly, because of the gelatin influence.

Rheology Testing

Gels of 8% gelatin content and 2% carbomer 974 were subjected to rheological testing. The appropriate tests are the oscillatory, non-destructive tests which are reported here in terms of the tan delta or loss tangent. This parameter is the ratio of the viscous and elastic moduli and consequently a value of unity indicates that the contributions from each of these is equal. A value of greater than one means that the material has become more liquid in character. Therefore stress and frequency sweeps are done with the intention of assessing the tan delta profiles.

Results are shown in FIGS. 15a-f. In these graphs, the profiles have been measured across both stress and frequency giving three-dimensional plots that clearly indicate chymotrypsin activity in terms of raised tan deltas, particularly at higher stress values, these being very much lower at zero enzyme content. The exception to this is at temperatures are raised above 37° C., the temperature at which gelatin melts. Thus, at 37° C., this system would be ineffective since the material would already be very softened without enzyme.

Fortunately, skin temperature is around 32° C., where the effect is as visible as at 20° C.

This test, with an enzyme very similar to stratum corneum chymotryptic enzyme (SCCE) found over-expressed in psoriatic plaque, suggests that the material would lose viscosity selectively over plaque and not over normal tissue, much as it has done in these artificial conditions. The diffusibility of drugs through the gelatin-rich phase (i.e. the interstitial regions of the material), is related to the viscosity there and the conclusion is that delivery of drug would be raised in areas over abnormal skin.

The disclosures of each patent, patent application and publication cited or described in this document are hereby incorporated herein by reference, in their entirety.

While the foregoing specification has been described with regard to certain preferred embodiments, and any details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. A gel system comprising Concanavalin A and dextran gel-forming moieties, stabilized by a network comprising a plurality of acrylic polymer backbones, formed by copolymerizing methacrylate derivatives of Concanavalin A and dextran, wherein 1) the polymer backbones are permanently cross-linked through one or more dextran moieties; and 2) pendant Concanavalin A and dextran moieties are appended to the backbones, and the pendant moieties are reversibly cross-linked, such that reversible binding controls viscosity of the gel system;

wherein in absence of an analyte, all permanent and reversible cross-linkages are present and the gel system is a viscous liquid, but in presence of analyte, the reversible-cross-links between the pendant moieties are reversed, effecting increasing permeability corresponding to increasing concentration levels of analyte.

2. The gel system of claim 1, in combination with a semi-permeable or permeable membrane.

* * * * *